US011286503B2

(12) United States Patent
Covas et al.

(10) Patent No.: US 11,286,503 B2
(45) Date of Patent: Mar. 29, 2022

(54) PROCESS FOR MODIFYING HUMAN CELL LINES TO PRODUCE FACTOR VII

(71) Applicant: FUNDAÇÃO HEMOCENTRO DE RIBEIRÃO PRETO—FUNDHERP, São Paulo (BR)

(72) Inventors: Dimas Tadeu Covas, São Paulo (BR); Marcela Cristina Corrêa de Freitas, São Paulo (BR); Virginia Picanço e Castro, São Paulo (BR); Kamilla Swiech, São Paulo (BR)

(73) Assignee: FUNDAÇÃO HEMOCENTRO DE RIBEIRÃO PRETO—FUNDHERP

( * ) Notice: Subject to any disclaimer, the term of this patent is extended or adjusted under 35 U.S.C. 154(b) by 0 days.

(21) Appl. No.: 16/786,576

(22) Filed: Feb. 10, 2020

(65) Prior Publication Data

US 2020/0347406 A1 Nov. 5, 2020

Related U.S. Application Data

(63) Continuation-in-part of application No. 15/577,212, filed as application No. PCT/BR2016/000041 on Apr. 27, 2016, now Pat. No. 10,590,405.

(30) Foreign Application Priority Data

May 27, 2015 (BR) .......................... 1020150123345

(51) Int. Cl.
*C12N 9/64* (2006.01)
*C12N 15/86* (2006.01)
*C12N 7/00* (2006.01)
*C12P 21/02* (2006.01)

(52) U.S. Cl.
CPC .............. *C12N 15/86* (2013.01); *C12N 7/00* (2013.01); *C12P 21/02* (2013.01); *C12N 2511/00* (2013.01); *C12N 2740/15042* (2013.01); *C12N 2740/15043* (2013.01)

(58) Field of Classification Search
None
See application file for complete search history.

(56) References Cited

U.S. PATENT DOCUMENTS

| | | | | |
|---|---|---|---|---|
| 4,784,950 | A | 11/1988 | Hagen et al. | 435/68 |
| 6,114,146 | A | 9/2000 | Herlitschka et al. | 435/69.7 |
| 6,265,183 | B1 | 7/2001 | Dorner et al. | 435/69.1 |
| 6,329,176 | B1 | 12/2001 | Woeldike et al. | 435/69.6 |
| 8,426,128 | B2 | 4/2013 | Stafford | 435/6.1 |
| 8,940,504 | B2 | 1/2015 | Streenstrup et al. | 435/69.1 |
| 10,590,405 | B2 * | 3/2020 | Covas | C12N 9/6437 |
| 2004/0023333 | A1 | 2/2004 | Hauser et al. | 435/69.6 |
| 2004/0185535 | A1 | 9/2004 | Wilson et al. | 435/69.6 |
| 2009/0075331 | A1 | 3/2009 | Knudsen | C12P 21/06 |
| 2009/0088370 | A1 | 4/2009 | Winge | 514/8 |
| 2010/0172891 | A1 | 7/2010 | Fontes et al. | 424/94.5 |
| 2010/0331255 | A1 | 12/2010 | Wallin | 514/13.7 |
| 2012/0282687 | A1 | 11/2012 | Koh et al. | 435/320.1 |
| 2014/0051122 | A1 | 2/2014 | De Souza Russo Carbolante et al. | 435/69.6 |
| 2017/0096684 | A1 | 4/2017 | Alton | |

FOREIGN PATENT DOCUMENTS

| | | | |
|---|---|---|---|
| WO | WO0170763 | 9/2001 | ........... C07K 14/745 |
| WO | WO02/29084 | 4/2002 | ............. C12P 21/02 |
| WO | WO 2006/067116 | 6/2006 | ............... C12N 9/64 |
| WO | WO 2007/065173 | 6/2007 | ............. C12N 15/09 |

OTHER PUBLICATIONS

U.S. Appl. No. 15/577,212, filed Feb. 8, 2018, Covas et al.
Chu et al. Inudstrial Choices for protein production by large-scale cell culture, Current Opinion in Biotechnology, 2001, 12:180-187.
Dumont et al. Human cell lines for biopharmaceutical manufacturing; History, status, and Future perspectives, Crit Rev Biotechnol, 2016, 36(6): 1110-1122.
European Search Report issued in corresponding European Appln. No. 16798970.6-1111 dated Mar. 28, 2018 (11 pgs).
Goh et al. Impact of host cell line choice on glycan profile, Critical Reviews in Biotechnology, 2018, vol. 38, No. 6, pp. 851-867.
International Preliminary Report on Patentability (w/translation) issued in application No. PCT/BR2016/000041, dated Nov. 28, 2017 (17 pgs).
International Search Report and Written Opinion (w/translation) issued in application No. PCT/BR2016/000041, dated Jul. 14, 2016 (27 pgs).
Jazayeri et al. Vector and Cell Line Engineering Technologies Toward Recombinant Protein Expression in Mammalian Cell Lines, Appl. Biochem. Biotechnol (2018) 185:986-1003.
Kumar et al., Industrial production of clotting factors: Challenges of expression, and choice of host cells, Biotechnol. J. 2015, 10, pp. 1-10.
Lu et al., Sequence-Modified Antibiotic Resistance Genes Provide Sustained Plasmid-Mediated Transgene Express in Mammals, American Society of Gene & Cell Therapy, Molecular Therapy, vol. 25, No. 5, May 2017, pp. 1187-1198 with Supplemental Information (8 pgs).

(Continued)

Primary Examiner — Hope A Robinson
(74) Attorney, Agent, or Firm — Hayes Soloway P.C.

(57) ABSTRACT

A process for producing blood coagulation Factor VII in large scale in 3 human cell lines (HepG2, Sk-Hep, and HKB-11) and to select the best recombinant protein producer is described. The murine line BHK-21 was used as control. The data allowed for the assertion that the system used to modify cell lines was efficient, so that all the cells were satisfactorily modified, and produced the protein of interest in a stable form. In addition, when comparing the murine line BHK-21 with the human cells (HepG2, Sk-Hep-1 and HKB-11), the latter proved to be able to produce rFVII more efficiently, which allows us to conclude that human cell lines are a great alternative to produce recombinant blood coagulation factors in large scale.

12 Claims, 18 Drawing Sheets

Specification includes a Sequence Listing.

(56) References Cited

OTHER PUBLICATIONS

Mei et al., "Expression of human coagulation factor VIII in a human hybrid cell line, HKB11," Molecular Biotechnology, Oct. 2006, vol. 34, No. 2, pp. 165-178 (11 pgs).
Spencer, H. Trent et al. "Lentiviral Vector Platform for Production of Bioengineered Recombinant Coagulation Factor VII" *Molecular Therapy* vol. 19, No. 2, 302-306 Feb. 2011 (8 pgs).
Swiech et al., Human cells: New Platform for recombinant therapeutic protein production, Protein Expression and Purification 84 (2012) 147-153.
Swiech, K. et al. Recombinant glycoprotein production in human cell lines. Methods Mol Biol. Janeiro de 2015. vol. 1258, pp. 223-240. doi: 10.1007/978-1-4939-2205-5J2. Abstract, pp. 229 and 233 to 239 (subitems 3.2 to 3.6).
Wajih, N. et al. Enhanced functional recombinant factor VII production by HEK 293 cells stably transfected with VKORCI where the gamma-carboxylase inhibitor calumenin is stably suppressed by shRNA transfection. Thromb Res. 2008. vol. 122, No. 3, pp. 405-410. doi: 0.1016/j.thromres.2007.11.002. Abstract, secao "Materiais e Metodos", first paragraph of section Results, Figure 2.

\* cited by examiner

A

Seq ID 01

ATGGTCTCCCAGGCCCTCAGGCTCCTCTGCCTTCTGCTTGGGCTTCAGGGCTGCCTGGCTGCAGTCTTCGTA
ACCCAGGAGGAAGCCCACGGCGTCCTGCACCGGCGCCGGCGCGCCAACGCGTTCCTGGAGGAGCTGCGGCCG
GGCTCCCTGGAGAGGGAGTGCAAGGAGGAGCAGTGCTCCTTCGAGGAGGCCCGGGAGATCTTCAAGGACGCG
GAGAGGACGAAGCTGTTCTGGATTTCTTACAGTGATGGGGACCAGTGTGCCTCAAGTCCATGCCAGAATGGG
GGCTCCTGCAAGGACCAGCTCCAGTCCTATATCTGCTTCTGCCTCCCTGCCTTCGAGGGCCGGAACTGTGAG
ACGCACAAGGATGACCAGCTGATCTGTGTGAACGAGAACGGCGGCTGTGAGCAGTACTGCAGTGACCACACG
GGCACCAAGCGCTCCTGTCGGTGCCACGAGGGGTACTCTCTGCTGGCAGACGGGGTGTCCTGCACACCCACA
GTTGAATATCCATGTGGAAAAATACCTATTCTAGAAAAAAGAAATGCCAGCAAACCCAAGGCCGAATTGTG
GGGGGCAAGGTGTGCCCCAAAGGGGAGTGTCCATGGCAGGTCCTGTTGTTGGTGAATGGAGCTCAGTTGTGT
GGGGGGACCCTGATCAACACCATCTGGGTGGTCTCCGCGGCCCACTGTTTCGACAAAATCAAGAACTGGAGG
AACCTGATCGCGGTGCTGGGCGAGCACGACCTCAGCGAGCACGACGGGGATGAGCAGAGCCGGCGGGTGGCG
CAGGTCATCATCCCCAGCACGTACGTCCCGGGCACCACCAACCACGACATCGCGCTGCTCCGCCTGCACCAG
CCCGTGGTCCTCACTGACCATGTGGTGCCCCTCTGCCTGCCCGAACGGACGTTCTCTGAGAGGACGCTGGCC
TTCGTGCGCTTCTCATTGGTCAGCGGCTGGGGCCAGCTGCTGGACCGTGGCGCCACGGCCCTGGAGCTCATG
GTCCTCAACGTGCCCCGGCTGATGACCCAGGACTGCCTGCAGCAGTCACGGAAGGTGGGAGACTCCCCAAAT
ATCACGGAGTACATGTTCTGTGCCGGCTACTCGGATGGCAGCAAGGACTCCTGCAAGGGGGACAGTGGAGGC
CCACATGCCACCCACTACCGGGGCACGTGGTACCTGACGGGCATCGTCAGCTGGGGCCAGGGCTGCGCAACC
GTGGGCCACTTTGGGGTGTACACCAGGGTCTCCCAGTACATCGAGTGGCTGCAAAAGCTCATGCGCTCAGAG
CCACGCCCAGGAGTCCTCCTGCGAGCCCCATTTCCCTAG

B 

Figure 1

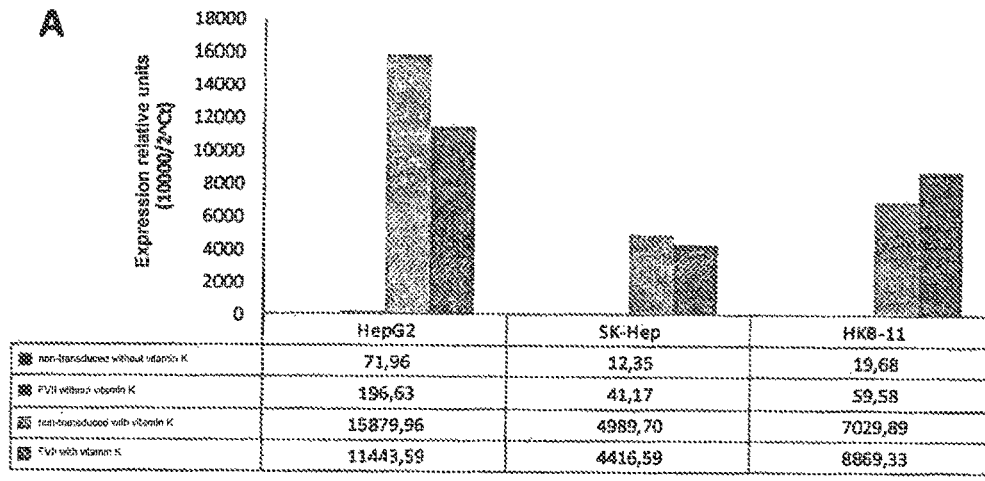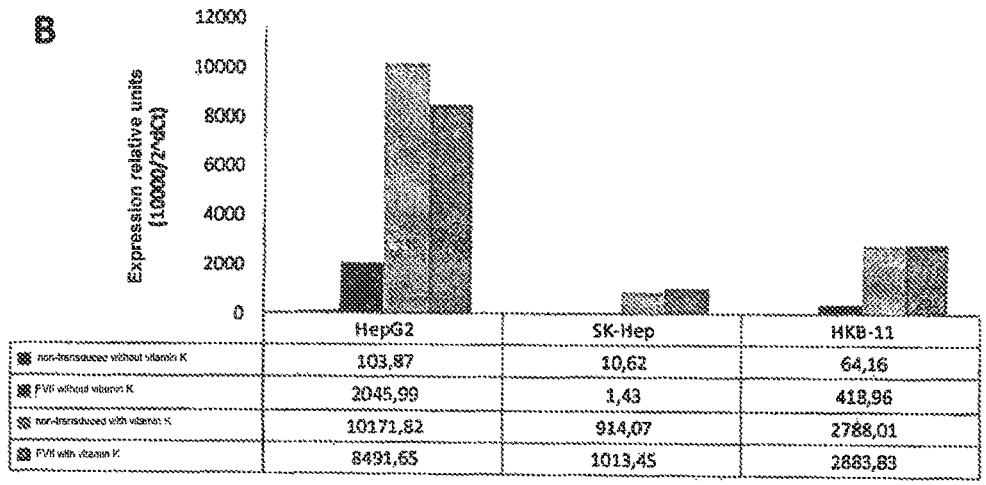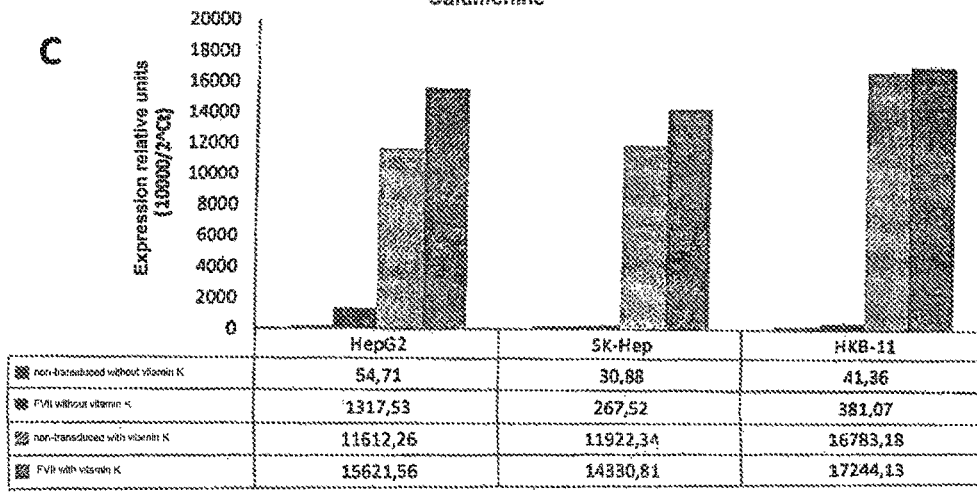
Figure 11

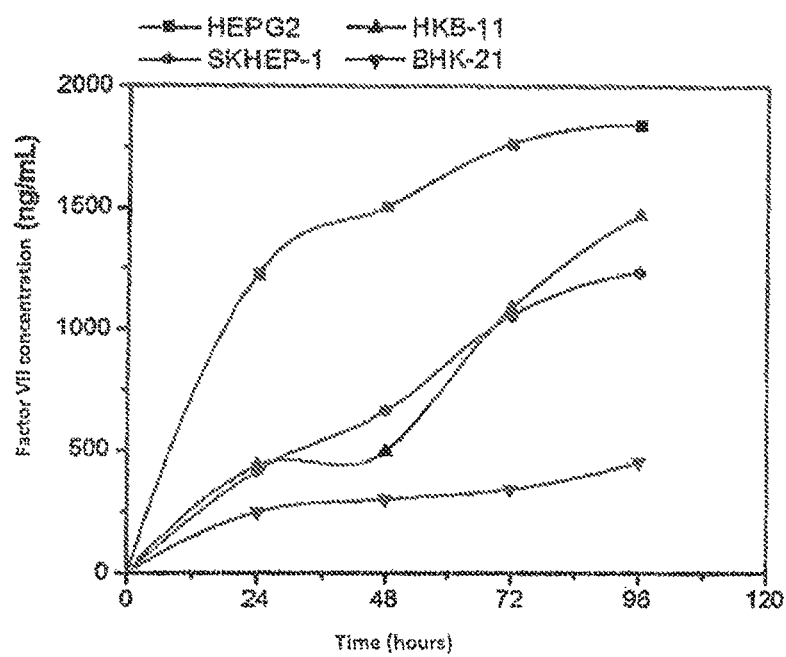
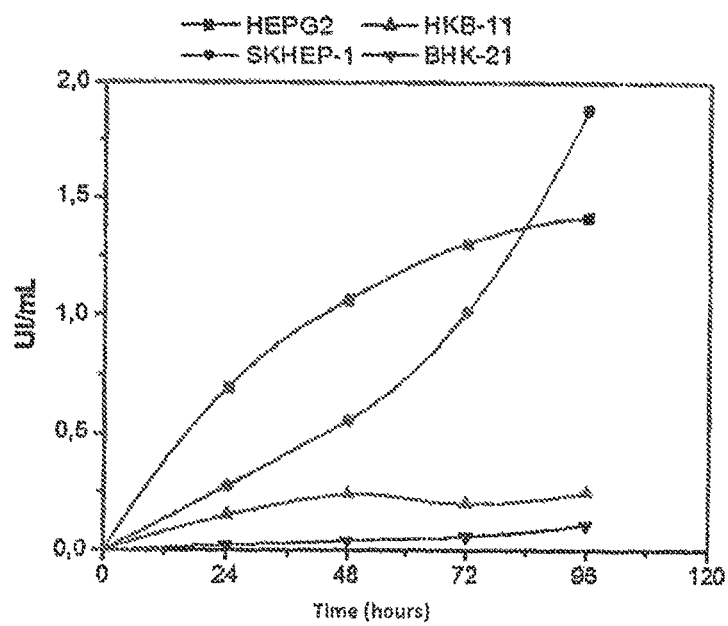
Figure 16

SEQUENCE LISTING

<160> NUMBER OF SEQ ID NOS: 1

<210> SEQ ID NO 1
<211> LENGTH: 1335
<212> TYPE: DNA
<213> ORGANISM: Homo sapiens

<400> SEQUENCE: 1

```
atggtctccc aggccctcag gctcctctgc cttctgcttg ggcttcaggg ctgcctggct      60
gcagtcttcg taacccagga ggaagcccac ggcgtcctgc accggcgccg gcgcgccaac     120
gcgttcctgg aggagctgcg gccgggctcc ctggagaggg agtgcaagga ggagcagtgc     180
tccttcgagg aggcccggga gatcttcaag gacgcggaga ggacgaagct gttctggatt     240
tcttacagtg atgggggacca gtgtgcctca agtccatgcc agaatggggg ctcctgcaag     300
gaccagctcc agtcctatat ctgcttctgc ctccctgcct tcgagggccg gaactgtgag     360
acgcacaagg atgaccagct gatctgtgtg aacgagaacg gcggctgtga gcagtactgc     420
agtgaccaca cgggcaccaa gcgctcctgt cggtgccacg aggggtactc tctgctggca     480
gacggggtgt cctgcacacc cacagttgaa tatccatgtg gaaaaatacc tattctagaa     540
aaaagaaatg ccagcaaacc ccaaggccga attgtggggg gcaaggtgtg ccccaaaggg     600
gagtgtccat ggcaggtcct gttgttggtg aatggagctc agttgtgtgg ggggaccctg     660
atcaacacca tctgggtggt ctccgcggcc cactgtttcg acaaaatcaa gaactggagg     720
aacctgatcg cggtgctggg cgagcacgac ctcagcgagc acgacgggga tgagcagagc     780
cggcgggtgg cgcaggtcat catccccagc acgtacgtcc cgggcaccac caaccacgac     840
atcgcgctgc tccgcctgca ccagcccgtg gtcctcactg accatgtggt gccctctgc     900 ctgcccgaac ggacgttctc tgagaggacg ctggccttcg tgcgcttctc attggtcagc     960
ggctggggcc agctgctgga ccgtggcgcc acggccctgg agctcatggt cctcaacgtg    1020
ccccggctga tgacccagga ctgcctgcag cagtcacgga aggtgggaga ctccccaaat    1080
atcacggagt acatgttctg tgccggctac tcggatggca gcaaggactc ctgcaagggg    1140
gacagtggag gcccacatgc cacccactac cggggcacgt ggtacctgac gggcatcgtc    1200
agctggggcc agggctgcgc aaccgtgggc cactttgggg tgtacaccag ggtctcccag    1260
tacatcgagt ggctgcaaaa gctcatgcgc tcagagccac gccaggagt cctcctgcga    1320 gccccatttc cctag                                                    1335
```

PROCESS FOR MODIFYING HUMAN CELL LINES TO PRODUCE FACTOR VII

CROSS REFERENCE TO RELATED APPLICATIONS

This application is a continuation in part of U.S. application Ser. No. 15/577,212, file Nov. 27, 2017, as a 371 of PCT Application PCT/BR2016/000041, filed Apr. 27, 2016, now U.S. Pat. No. 10,590,405, granted Mar. 17, 2020, the contents of which are incorporated herein by reference in their entirety.

FIELD OF THE INVENTION

The present invention is within the scope of application of Chemistry, Pharmacy, Medicine, Biotechnology and, more specifically, in the field of preparations for medical purposes since it relates to the process of producing blood coagulation factor VII in large scale in human cell lines using static conditions and/or in suspension using microcarriers.

BACKGROUND OF THE INVENTION

Coagulopathies

Hemophilia A is a blood disease linked to the X chromosome, caused by a deficiency or abnormality of factor VIII (FVIII), a cofactor necessary for the generation of fibrin. This deficiency of the coagulation protein is the most common disorder among coagulopathies, with an incidence of approximately 1 in 5,000 males and is currently affecting approximately 400,000 people worldwide. Hemophilia B is a hereditary disease that is also associated with the X chromosome and consists of the deficiency of blood coagulation factor IX, with an incidence of 1 in every 30,000 males. Clinically, both hemophilia A and B present many similarities, that is, the patient presents frequent bleeding episodes, most of the time in cutaneous, musculoskeletal and soft tissue regions. Bleeding can also occur in other critical regions, such as, for example, intracranial or retroperitoneal spaces.

Conventional therapy for patients with hemophilia consists of intravenous infusion of factor VIII or FIX derived from plasma or recombinant protein. However, one of the major problems is the formation of inhibitory antibodies against FVIII and FIX, which is currently, the most significant treatment-related complication in the clinical attendance of hemophiliac patients. Approximately 5% of patients with hemophilia B and 20 to 30% of patients with severe hemophilia A, submitted to FIX and FVIII replacement therapy, respectively, develop antibodies that inhibit the activity of the infused factor. The treatments available for these patients include the use of hemostatic agents and the induction to immunologic tolerance using high doses of FVIII or FIX infusions. These approaches are expensive because of the high cost of the factors, and not always successful. For this reason, many efforts have been made to find a hemostatic effective treatment, independent of the presence of factor VIII and IX.

Over the years, many studies have identified activated factor VII (FVIIa) as an attractive candidate for hemostasis, regardless of the use of FVIII/FIX in animals with hemophilia models. In addition, the FVIIa purified from plasma has been shown to induce hemostasis in some patients suffering severe hemophilia. Taken together, these data suggest that pharmacological doses of FVIIa bound to the tissue factor (TF) exposed in the injury site, activate FX and promote the formation of thrombin in the injury site, causing this coagulation factor to present itself as an alternative for hemophiliac patients with inhibitory antibodies.

Mechanisms of Action of FVII in Normal Hemostasis and the Role of Pharmacological Doses According to the current concept, hemostasis occurs in two major types of surface: the cells that express tissue factor (TF) and platelets activated by thrombin and is initiated by the formation of a complex between the exposed TF and the FVIIa present in the circulation. FVII/FVIIa is the natural ligand of the tissue factor and the formed complex is fairly strong and stable.

Once the complex between TF and FVIIa is formed, the formation of a limited amount of thrombin occurs. This limited number of thrombin molecules formed in the initial phase of hemostasis activates the cofactors FVIII, FV, FXI, and the platelets. Once activated, the platelets leave the circulation and go to the injury site. The activation of factors VIII and IX on the surface of activated platelets promotes activation of factor X in FXa, which in turn binds to FVa generating a large amount of thrombin. The final step in the process is of a firm fibrin clot, which is resistant to premature proteolysis and is capable not only of initiating but also of maintaining homeostasis, while the healing process is established.

In the absence of FVIII or FIX, only a small amount of thrombin is generated by the TF-FVIIa complex and the generation of total thrombin, which begins on the surface of platelets, does not occur. This last phase depends on the formation of the FVIII-FIX complex on the surface of the activated platelets. As a result, fibrin clots formed in hemophiliac patients are fragile and easily dissolved by premature proteolysis. From studies of hemophilia in cellular models, it was possible to demonstrate that pharmacological concentrations of recombinant factor VIIa (rFVII) bind nonspecifically to activated platelets and generate thrombin on the surface thereof, even in the absence of FVIII/FIX. This occurs because rFVIIa activates FX on the surface of activated platelets independent of the presence of FVIII or FIX.

In this way, the addition of pharmacological doses of rFVIIa results in a rapid increase in the rate of thrombin generation on the activated platelet surface and as a result of increased activation of the platelets at the site of injury increased adhesion of platelets were observed, as well as other mechanisms necessary to maintain the homeostasis.

On Mar. 25, 1999, the FDA (Food and Drug Administration) approved the use of the first and only recombinant factor VII, NovoSeven®. Distributed by NovoNordisK, the recombinant activated factor VII (rFVIIa) is indicated in the treatment of bleeding episodes for patients with hemophilia A and B who develop antibodies against factors VIII and IX, respectively. Also, rFVIIa is recommended for the treatment of critical spontaneous and/or surgical bleeding which threatens the lives of patients, as well as in patients with other diseases such as FVII deficiency and Glanzmann's thrombasthenia.

Factor VII Gene

The factor VII gene has its locus located in region 34 of the long arm of chromosome 13 (13q34). Structurally and functionally, they are related to the group of vitamin K dependent serine proteases, which include factors IX, X, prothrombin (FII) and protein C. Its size is approximately 12.8 Kb and it is composed of nine axons and eight introns. The nucleotide sequence of the exons is fully known. It is known that exons 1a and 1b and part of exon 2 encode a peptide signal that is removed during processing. The rest of the exon 2 and axons 3 to 8 encode a protein of 406 amino acids present in the blood circulation.

FVII is synthesized in the liver and circulates in the blood at a concentration of 0.5 µg/ml as a single chain, with a molecular weight of 50 kDa. In the amino-terminal moiety, it consists of a domain rich in glutamic and γ-carboxylated acid (GLA domain), followed by two domains similar to epidermal growth factor (EGF), a short binding peptide and a serine protease domain in the carboxy-terminal moiety.

The conversion of factor VII into the active enzyme (FVIIa) occurs through the cleavage of the Arg152-Ile153 peptide bond, in which no release of any peptide occurs. Consequently, factor VIIa is composed of two polypeptide chains joined by a disulfide bond. The light chain is comprised of the GLA domain, the aromatic helix, and two EGF domains. This chain is composed of 152 amino acids that encode a protein of 20 kDa molecular weight. The heavy chain contains the catalytic site of the molecule and is comprised of 254 amino acids with about 30 kDa molecular weight.

Factor VII and Vitamin K Dependent γ-Carboxylation

One of the main problems with the production of vitamin K-dependent recombinant coagulation factors for therapeutic use has been the deficient functional recovery of these proteins of the cell culture medium. Prior art references have shown that these results are mainly due to 1) the incomplete γ-carboxylation of secreted proteins and 2) inefficient removal of the propeptide by furin protease in the Golgi complex.

The vitamin K-dependent γ-carboxylation system is a system composed of several proteins located on the membrane of the endoplasmic reticulum. It consists of 1) a vitamin K-dependent γ-carboxylase enzyme, which requires the reduced form of hydroquinone of vitamin K (vit. K1H2) as a cofactor and 2) the warfarin-sensitive enzyme, vitamin K 2,3-epoxide reductase (VKOR), which produces the cofactor. Concomitant with γ-carboxylation, hydroquinone is converted into the metabolite vitamin K 2,3 epoxide which is reduced back to the vit. K1H2 cofactor by the action of VKOR, in the so-called vitamin K cycle.

The calumenine protein was identified as one of the factors capable of regulating the γ-carboxylation system, wherein the same would bind γ-carboxylase as an inhibitory chaperone and would also affect the VKOR protein. This conclusion is based on data that include: 1) the inhibition of γ-carboxylase activity with transfection of a construct containing the calumenine cDNA, 2) the silencing of the calumenine gene by a Smart siRNA and 3) a proteomic approach that demonstrates the existence of protein-protein interactions between γ-carboxylase and calumenine. It has also been shown that when using Hek293 cells there was an increase in the production of recombinant FVII in these cells of 9% to 68% when they were transfected for superexpression of the VKORC1 protein and concomitantly had the calumenine gene stably suppressed by more than 80% by the expression of an shRNA.

Within this context, it is possible to predict that a human cell line has the proper machinery to make translation modifications, such as γ-carboxylation and more efficiently produce recombinant FVII.

STATE OF THE ART

Documents US 2004023333, US 2010172891, BRPI 1105317-8 and "Expression of human coagulation factor VIII in a human hybrid cell line, HKB11" discloses the production of FVIII, different from the present invention which describes the production of FVII. It is worth noting that despite both participate in the blood coagulation cascade, factors VII and VIII are proteins that have different post-translational modifications and are classified into different protein families.

Document U.S. Pat. No. 4,784,950 describes the production of proteins from artificial plasmid constructs that combine part of the protein of interest and part of factor VII. The present invention is directed to the production of FVII and the construction of the recombinant DMA using the FVII in its entirety. The cited document uses murine (BHK) cells while the invention uses human cell lines.

Document US 2009088370 has the objective of increasing the secretion of the target proteins from the modification of the cultivation conditions. In this document it is reported that the cells are cultivated in specific conditions of serum-free medium with the addition of substances to the culture medium, these being mainly ionic substances. In the present invention, commercial media are used, chemically defined, with or without the addition of bovine fetal serum. Cells cited by the document: 293, 293T, 293F, 293H, Cos, CHO, NS0, insect cells. It does not mention any of the human cell lines used in the present invention.

Document US 2010331255 has as its main objective the increase in the expression of the target protein by manipulating the cell gamma-carboxylation system. Document US 2010331255 uses FIX as the principal protein and is concomitant with the expression of the target protein, the VKORC1 gene is overexpressed and inhibits the inhibitory gene calumenine, using siRNA, in mouse cells (BHK). In the present invention, although the expression of the proteins bound to the gamma-carboxylation process is quantified, no methodology was used to intervene in the natural process of the cells.

Objectives and Advantages of the Invention

The present invention refers to a method of modifying human cell lines with a lentiviral vector containing blood coagulation FVII cDNA and develop a bioprocess that enables the large-scale production of FVII using human cells.

The present invention developed the use of human cell lines to produce rFVII more efficiently and because human cells are used, the development of immunogenic epitopes expressed in murine cells is avoided. The calumenine protein was identified as one of the factors capable of regulating the g-carboxylation system thus obtaining a safer recombinant product. The use of murine cell lines has disadvantages if we consider the complexity of post-translational modifications of FVII.

BRIEF DESCRIPTION OF THE INVENTION

The present invention relates to the process of producing blood coagulation factor VII in 3 human cell lines (HepG2, Sk-Hep, HKB-11). The murine BHK-21 line was used as a control. Initially, the partial FVII mRNA form variant 2 (Seq ID 01, FIG. 1(A)) was cloned into the bicistronic lentiviral vector p1054-CIGWS (FIG. 1(B)), which contains a selectable marker, for example, a antibiotic resistance gene such as hygromycin or neomycin, or aminoglycoside phosphotransferase or bleomycin and its derivatives thereof i.e. phleo, bleo, zeocin, or Xanthine-guanine phosphoribosyltransferase and its derivatives thereof i.e. XGPRT, gpt, minonucleoside antibiotic such as puromycin and a GFP encoding a fluorescent protein, which allows for the observation of the transduction efficiency of cell lines. After modifying the cells, the expression of GFP was observed by fluorescence microscopy and flow cytometry, in which 80% of BHK-21-rFVII cells presented GFP expression. HepG2-rFVII cells showed an expression of 73% whereas HKB-11-rFVII cells showed 32% of cells were GFP positive. The Sk-Hep-rFVII cell line was the one that showed better transduction efficiency, with 95% of the cell population being GFP positive. Subsequently, rFVII produced by the modified cell lines was characterized. Protein quantification by the ELISA assays was done. The analyses showed that in 48 h of culture, HepG2/rFVII cells produced about 1506 ng/ml rFVII, followed by SKHep/rFVII (951 ng/ml), HKB-11/rFVII (808 ng/ml) and BHK-21/rFVII (302 ng/ml). The same cell supernatant was used to verify the amount of FVII produced that was biologically active. After the coagulometric test HepG2/rFVII cells were found to produce 1.07 IU/mL of biologically active rFVII, followed by SKHep/rFVII (0.56 IU/mL), HKB-11/rFVII (0.60 IU/mL) and BHK-21/rFVII (0.04 IU/mL) lines. To analyze the mRNA expression related to rFVII, as well as γ-carboxylation-related enzymes, a real-time PCR was performed. After analyzing the data, it was observed that the three modified human lines showed mRNA expression relative to rFVII. When undergoing treatment with vitamin K for a period of 10 passages in culture, rFVII gene expression was similar for the three lines (HepG2: 164563 ERU, HKB-11: 119122 ERU and Sk-Hep: 124919 ERU) which suggests that there was stabilization in the expression levels of the recombinant protein. Concerning γ-carboxylation enzymes, it was possible to observe that both γ-carboxylase, VKORC1, and the calumenine inhibitor presented increased levels of mRNA expression when treated with vitamin K, suggesting that it activates the enzymes of the cycle.

Our data showed that our vector can modify efficiently the human cells and stably produce the rFVII. In addition, comparing the murine BHK-21 line with human cells (HepG2, Sk-Hep-1, and HKB-11), the human cells can produce rFVII more efficiently. In conclusion, human cell lines are a great alternative to the production of recombinant blood coagulation factors, even in large-scale conditions.

BRIEF DESCRIPTION OF THE FIGURES

FIG. 1 shows the Seq ID 01 (A) of the partial FVII mRNA form variant 2 which was cloned into the bicistronic lentiviral vector p1054-CIGWS and (B) refers to the schematic representation of lentiviral vector p1054-CIGWS construction.

FIG. 11 graphically depicts the relative expression of mRNA recombinant Factor VII gene related to γ-carboxylase enzyme gene (A), VKORC1 (B) and calumenine inhibitory protein (C) in human cell lines HepG2, HKB-11 and Sk-Hep FIG. 12 graphically depicts the relative expression of mRNA related to γ-carboxylase enzyme gene (A), VKORC1 (B) and calumenine inhibitory protein (C) in human cell lines HepG2, Sk-Hep-1 and HKB-11, before and after transduction, before and after treatment with vitamin K.

FIG. 16 graphically depicts the production kinetics of the recombinant factor VII producing cell lines quantification performed by (A) ELISA and (B) partial thromboplastin time (PTT) method, FIG. 17 graphically depicts the culture of the cell line Sk-Hep-FVIIr in microcarriers in spinner flasks in DMEM medium 10% FBS (n=2)—cell growth (A), specific maximum growth rate (B) and concentration profile of glucose and lactate during culture (C).

DETAILED DESCRIPTION OF THE INVENTION

Figure 2:
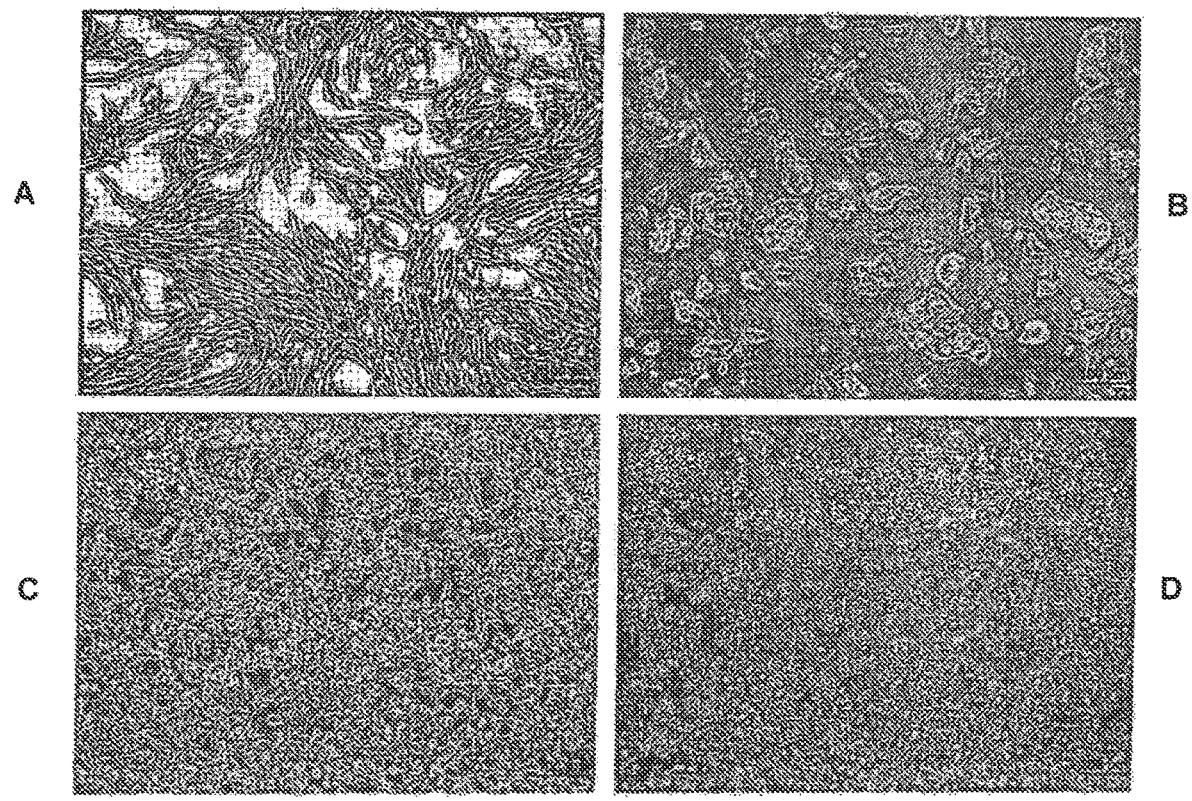
FIG. 2 shows the morphology of human cell lines—Phase-contrast imaging of (A) BHK-21 cell line, (B) HepG2 cell line, (C) HKB-11 cell line and (D) Sk-Hep-1 cell line.

The present invention describes the process of producing recombinant blood coagulation factor VII, which consist of the following steps:

1) Obtaining virus particles containing FVII and the GFP protein as reporter gene—using lentiviral vector;
2) Transducing human cell lines, preferably, SK-Hep 1, HKB 11, and HepG 2 with viral particles to form FVII-producing cells;
3) Culturing human FVII-producing cells in suspension using culture flasks, spinner flasks or bioreactors.

Transfection of the Hek293T cell line to produce viral particles was performed. For viral production, it is important that the cell line (Hek293T) stably expresses the gene for the large SV40 T antigen. In this process it is necessary to use a vector containing the transgene and two auxiliary vectors, which have the origin of replication of SV40 so that after transfection the plasmids within, the cells can replicate, this then increases transcription of the transgene and the production of viral proteins and ultimately viral particles will be secreted into the culture medium.

For the production of viral particles, the reagents polyethylamine (PEI) and Lipofectamine® were used. The three plasmids were transfected into the following proportions: 10 to 20 μg vector with a transgene (p1054-rFVII), 8 to 15 μg pCMVΔR8.91 (containing HIV-1 gag, pol, rev, and tat), and 5 to 10 μg pMD2 VSVG (encodes the VSV-G shell).

After transfection (15 to 20 hours) the cells were incubated with fresh medium. After 48 hours the supernatant was collected, centrifuged at 450×g for 5 minutes at 4° C., and filtered (0.45 μm filter) for the removal of cell fragments. Aliquots of 1 ml were frozen at −80° C. for the determination of viral titer and use in transduction experiments. Once frozen at −80° C. and thawed (at 37° C.), the infection strength is decreased by about 20 to 40%.

For titration of the viral supernatant, $2 \times 10^5$ Hek293T cells were initially plated in each well of the 6-well plate. After reaching 80 to 90% confluence, the cells were infected with the supernatant containing the p1054-rFVII virus in the following dilutions: 1:1, 1:2 and 1:3. The dilutions were made in duplicate and 5.5 ug/mL of polybrene was used.

After 16 h of infection, the cell medium was changed to fresh medium (DMEM 10% fetal bovine serum). Cells were then cultured for 48 h and after this period was trypsinized and taken for flow cytometry for analysis of the expression of the GFP gene contained in vector p1054-rFVII. With the results obtained by the flow cytometry, it was possible to calculate the viral titer.

Factor VII and GFP are not fused, they are separated by an IRES element; the method is further comprised of identifying the transduced cells and non-transduced cells by the presence of the GFP protein.

The supernatant produced by Hek293T cells that were previously transfected and frozen was thawed and placed on the cultures of the Sk-Hep, HepG2, HKB11 and BHK, in the presence of 5.5 μg/ml polybrene. For this, 24 hours before of the transduction, the cells were plated at $2 \times 10^5$ cells per well in the 6-well plate. A virus concentration of 10 virus/cell was employed, based on the values obtained by viral titration. After the addition of the viral supernatant, the cells were incubated at 37° C. in a humid atmosphere containing 5% $CO_2$, and the transduction cycles were repeated for two to three consecutive days, depending on the cell line.

Initially, the cells were cultured in 75 $cm^2$ culture flasks for expansion and incubated at 37° C. and 5% $CO_2$. After reaching the confluence of approximately 80%, the cells were released with Trypsin-EDTA and inoculated in 75 $cm^2$ T-flasks. The cellular morphology during expansion was observed with the use of an inverted microscope.

After reaching a sufficient number of cells ($2 \times 10^5$ cells/mL), the cells were inoculated into a 150 mL spinner flask (working volume of 50 mL) or a 2 L stirred tank Bioreactor (working volume of 1 L) already containing culture medium and microcarriers. A concentration ranging from 2.0 to 4.0 g/L of CYTODEX 3 microcarrier was used. The preparation and sterilization of the microcarriers were performed according to the manufacturer's instructions. The experiment was divided into 2 phases: the phase for cell adhesion on microcarriers and the phase for cell expansion. The duration of the adhesion phase was 6 hours with intermittent agitation: every 30 minutes for 2 minutes. For the expansion phase, stirring at 40-50 rpm was used.

In order to evaluate the cell adhesion in the suspension cultures, samples were taken at each hour for cell density and viability determination.

To monitor cell growth during the expansion phase samples were taken every 24 hours for cell quantification and further analysis of glucose, glutamine, lactic acid and ammonia. Free cells in suspension were quantified using the tripan blue exclusion method. For the cells adhered to microcarrier, the quantification was determined using of the Crystal Violet method.

Samples of the cell supernatant were collected, centrifuged and frozen at −20° C. for further ELISA and biological activity assays.

The experiment lasted 7-10 days, and every 3 days photomicrographs were performed under phase contrast microscopy to analysis of the cells adhered on microcarriers and microscopy of fluorescence was performed, for analysis of GFP expression.

Adaptation Step to Serum-Free Medium

For the adaptation step, the HKB-11 cells were cultured in 75 cm$^2$ T-flasks in DMEM-F12 medium containing 10% fetal bovine serum. After reaching the confluence of 90%, the cells were trypsinized with a trypsin-EDTA solution and 1×10$^6$ cells were plated in 25 cm$^2$ T-flasks with serum-free medium supplemented with Pluronic, ITS (Insulin, Transferrin and Selenium) and 10% (v/v) Penicillin/Streptomycin. The serum free formulation can be supplemented with insulin and/or glutamine and/or ferric sulfate and/or synperonic and/or Insulin-Transferrin-Selenium and/or Sodium Pyruvate and/or Pluronic F68 and/or Lipid Supplement and/or Cholesterol Supplements and/or Amino Acid Solution and/or 2-Mercaptoethanol and/or its derivatives.

After 48 h, the cells were harvested, counted and viability was observed by trypan blue reagent (0.4%). Again 1×10$^6$ viable cells were plated in 25 cm$^2$ T-flasks with serum-free medium supplemented. This procedure was performed in 5 passages until the cells were adapted to the growth in serum-free medium.

When adapted cells were cultured in a bioreactor under controlled temperature, pH, dissolved oxygen and agitation conditions, the cells were able to secrete 45 times more recombinant FVII when compared to spinner flask culture. In the culture medium supplemented with fetal bovine serum, the yield was considerably lower.

This process produces about three times as much FVII protein than the amount of FVII protein normally found in human plasma.

Results

Characterization of Cell Lines

The human cell lines HepG2, Sk-Hep-1, HKB-11 and BHK-21 murine cell line, were cultured to produce a master cell bank and a working cell bank.

In order to better understand the cell lines used in the present invention, morphological characterization of the cells was performed by contrast of phase optical microscopy (FIG. 2).

As can be seen in FIG. 2, murine BHK-21 cells (A) are large, with elongated fibroblastic morphology. In B, it can be observed the HepG2 line which grows in clusters of cells adhered to the culture plate. This profile of growth is probably because these cells derive from a hepatocarcinoma.

The hybrid cell line HKB-11 as shown in (C), demonstrates that the cells grows adhered and have a more elongated morphology, however, they have a smaller size, when compared to BHK-21. The Sk-Hep-1 line (D) presents the morphology of epithelial cells, according to their original hepatic adenocarcinoma.

Figure 3:
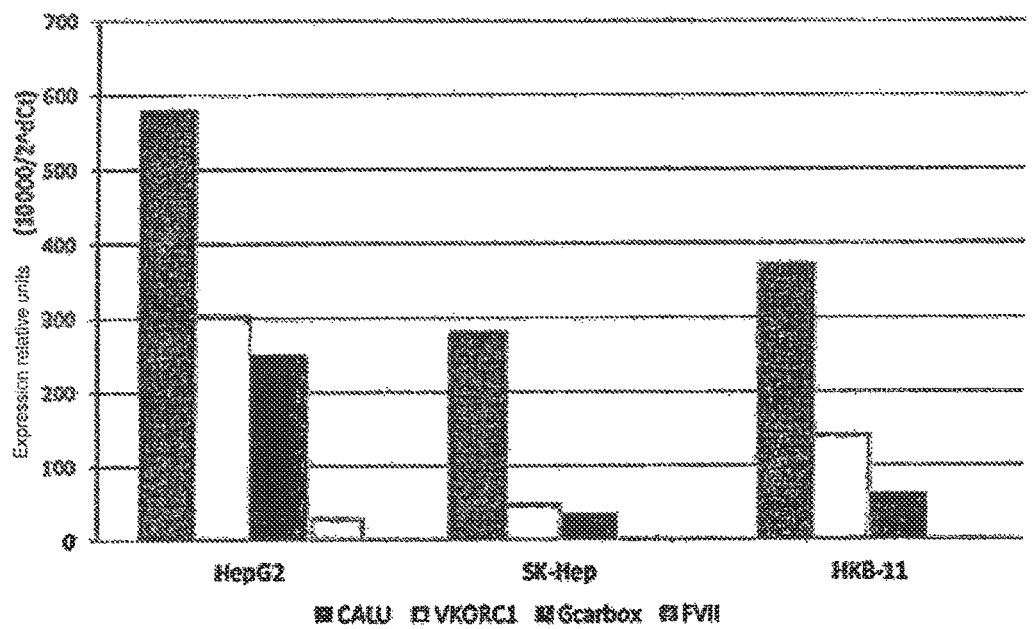
FIG. 3 shows the gene expression of CALU, VKORC1, γ-carboxylase and Factor VII in human cell lines.

Besides the morphological characterization, the human cell lines were also characterized in terms of gene expression involved in the γ-carboxylation process. For this, the real-time PCR quantification of β-carboxylase genes and vitamin K 2,3-epoxide reductase (VKORC1), in addition to the calumenine inhibitory gene (cALU) were also performed. The quantification of mRNA for the gene of endogenous Factor VII was also possible, as shown in FIG. 3.

Concerning the genes involved in the γ-carboxylation process, it was observed that γ-carboxylase and VKORC1 were the most expressed genes in HepG2 cell lines. HepG2 cells expressed 251 expression relative units (ERU) of the γ-carboxylase gene and 305 ERU of the VKORC1 gene. HKB-11 and SK-Hep cells expressed about 63 ERU and 35 ERU of γ-carboxylase gene and 144 ERU and 50 ERU of the VKORC1 gene, respectively.

As observed in the graphic, the HepG2 cell lines were the one which most expressed the inhibitory gene CALU, in the order of 580 ERU, followed by HKB-11 (371 ERU) and SK-Hep (281 ERU) lines.

In order to select the best cell line to produce recombinant factor VII, a ratio between the expression of the CALU inhibitory gene and the expression of the genes involved in γ-carboxylation was considered (Table 1).

TABLE 1

| | Ratio between the expression of CALU, VKORC1 and γ-carboxylase | |
|---|---|---|
| Cells | Ratio (CALU/VKORC1) | Ratio (CALU/γ-carbox) |
| HepG2 | 1.90 | 2.30 |
| SK-Hep | 5.54 | 7.85 |
| HKB-11 | 2.57 | 5.82 |

As shown in Table 1, the cell line that presented a lower ratio between the expression of the inhibitory gene CALU and the γ-carboxylase and VKORC1 was HepG2, followed by the HKB-11 line.

After the characterization of the human cell lines, the next step consisted of the cloning of the factor VII gene.

Factor VII is a gene that, through the process of alternative splicing, presents 4 variants with one of them not being transcribed. The prevalent form in the normal liver is variant 2, which was chosen to clone. The present invention employs the partial sequence of FVII variant 2 mRNA (FIG. 1). This was cloned in the expression vector p1054-CIGWS. Viral vectors have as main advantage the insertion of the transgene into the DNA of the host cell, with which it passes to stably express the gene of interest.

The lentiviral vector used in this invention has the WPRE element which increases the efficiency of mRNA transport and processing, which, in turn, probably contributed to a greater expression of FVII in the human cell lines.

Cloning of the FVII cDNA in a Lentiviral Vector

After cloning the FVII gene in the p1054 lentiviral vector, which culminated in the generation of p1054-rFVII vector, this vector was used to produce viral particles. To produce lentiviral particles in Hek293T cells in addition to the vector containing the transgene, two other vectors, pCMVΔR 8.91 and pMD2.VSVG, responsible for the formation of the capsid and viral envelope, respectively, are also required. All vectors used were checked with restriction enzymes for confirmation of integrity.

With the three vectors checked, the triple co-transfection of the Hek293T cell line to produce lentivirus using transfection reagents, such as PEI reagent was performed.

Since the p1054 vector has the green fluorescence protein gene, GFP, it was possible to verify the transfection efficiency of the cell line through fluorescence microscopy and flow cytometry.

Figure 4:
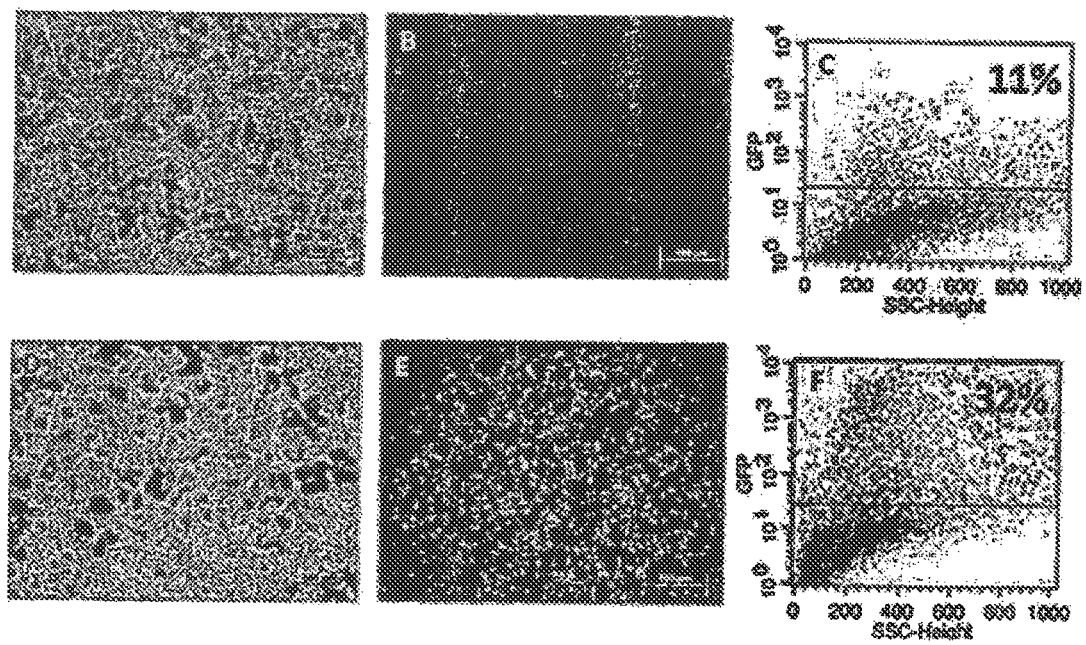
FIG. 4 shows transfection efficiency in Hek293T cells after 48 h using two different reagents: Lipofectamine® and PEI Phase—contrast imaging of transfected Hek293T cell line (A and D); Phase-contrast imaging of Hek293T cells after 48 h of transfection using Lipofectamine® (B) and PEI (E); in C and F the percentage of GFP positive cells was measured by flow cytometry.

FIG. 4 shows the photomicrography of Hek293T cells after 48 h of transfection with the PEI reagent and Lipofectamine®. The percentage of positive GFP cells detected by flow cytometry was 32.17% (FIG. 4F).

After the generation of the lentivirus producing Hek293T cell line, the next step consisted of collecting the cell supernatant containing the viral particles and titrating the amount of virus with an intention to know exactly how many viruses would be used in the next step, the transduction of target cell lines.

To do so, the protocol previously described was used. 3 different dilutions of the viral supernatant were used in duplicate. After 48 hours of infection, the cells were trypsinized and, since the p1054-rFVII vector has GFP, the percentage of infection can be observed by flow cytometry and subsequent calculation of viral titer.

Figure 5:
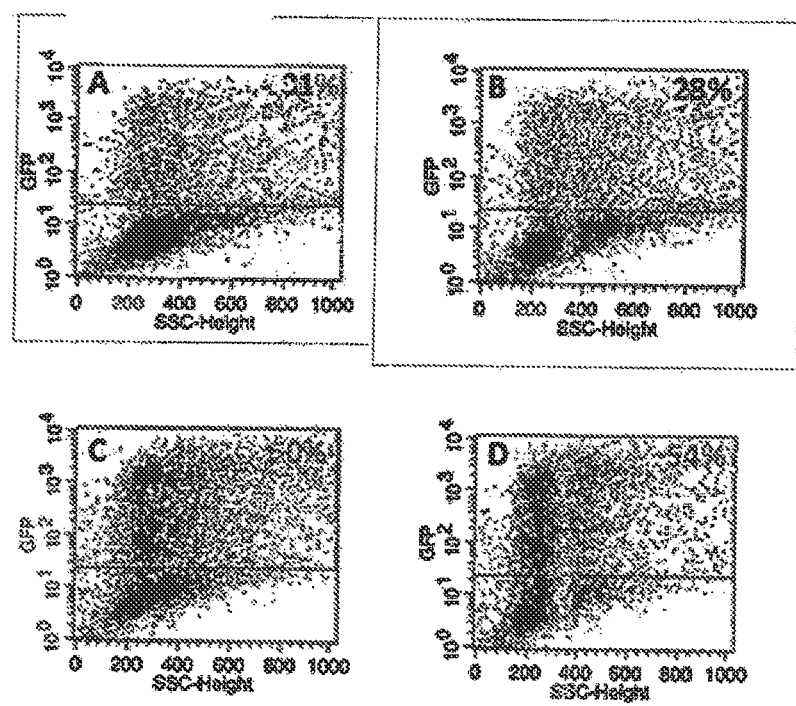
FIG. 5 shows the expression of GFP in Hek293T cells after 48 h of infection to calculate viral titer—Dilutions of viral supernatant—1:3 (A and B), 1:2 (C and D).

As can be seen from FIG. 5, it shows duplicates A and B, C and D relative to the dilutions of 1:3 and 1:2, respectively.

To calculate the viral titer, the values for the 1:3 dilution were used. The calculated viral titer was $2 \times 10^6$ virus/ml.

Modified Cell Lines for rFVII Production

Figure 6:
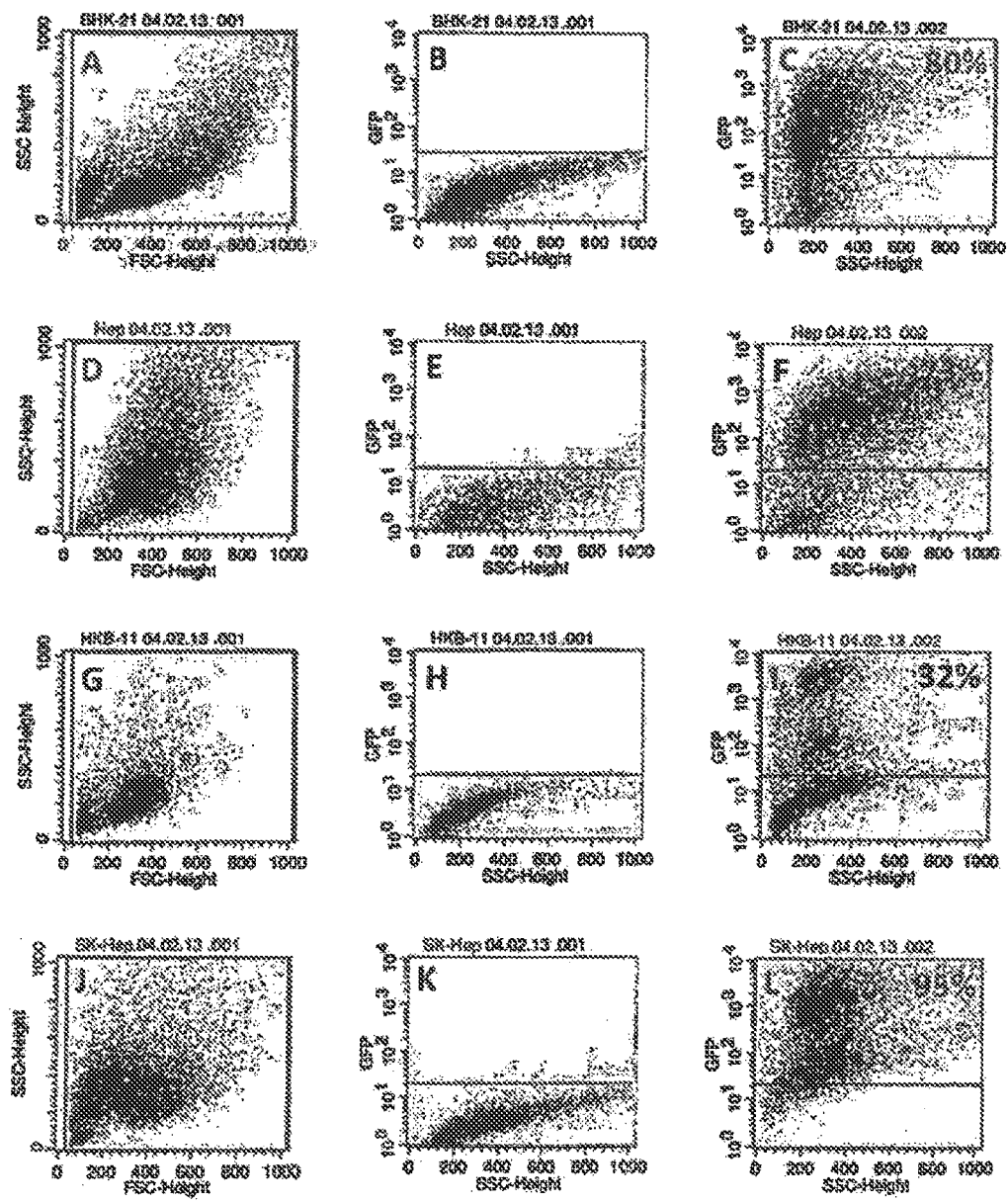
FIG. 6 graphically depicts the expression of GFP in recombinant cell lines BHK-21, HepG2, HKB-11, and Sk-Hep. The A, D, G and J dotplot showing size (FSC) by internal complexity (SSC) of the respective cells; The B, E, H and K dotplot showing the absence of GFP gene expression in control cells; The C, F, I and L dotplot showing GFP expression in cell lines modified with the vector p1054-rFVII.

After transduction with the viral supernatant, 4 cell lines modified with the vector p1054-rFVII were obtained, these being BHK-21 (murine), HepG2, Sk-Hep and HKB-11 (human). In order to verify if the modification had taken place satisfactorily, the expression of the GFP marker gene by flow cytometry was observed. As shown in FIG. 6, 80% of the BHK-21-rFVII cells presented GFP expression. HepG2-rFVII cells showed an expression of 73% whereas HKB-11-rFVII cells showed 32% of GFP. Sk-Hep-rFVII cell line was the one that showed the best efficiency of transduction, with approximately 95% of the cells expressing GFP after the modification.

Figure 7:
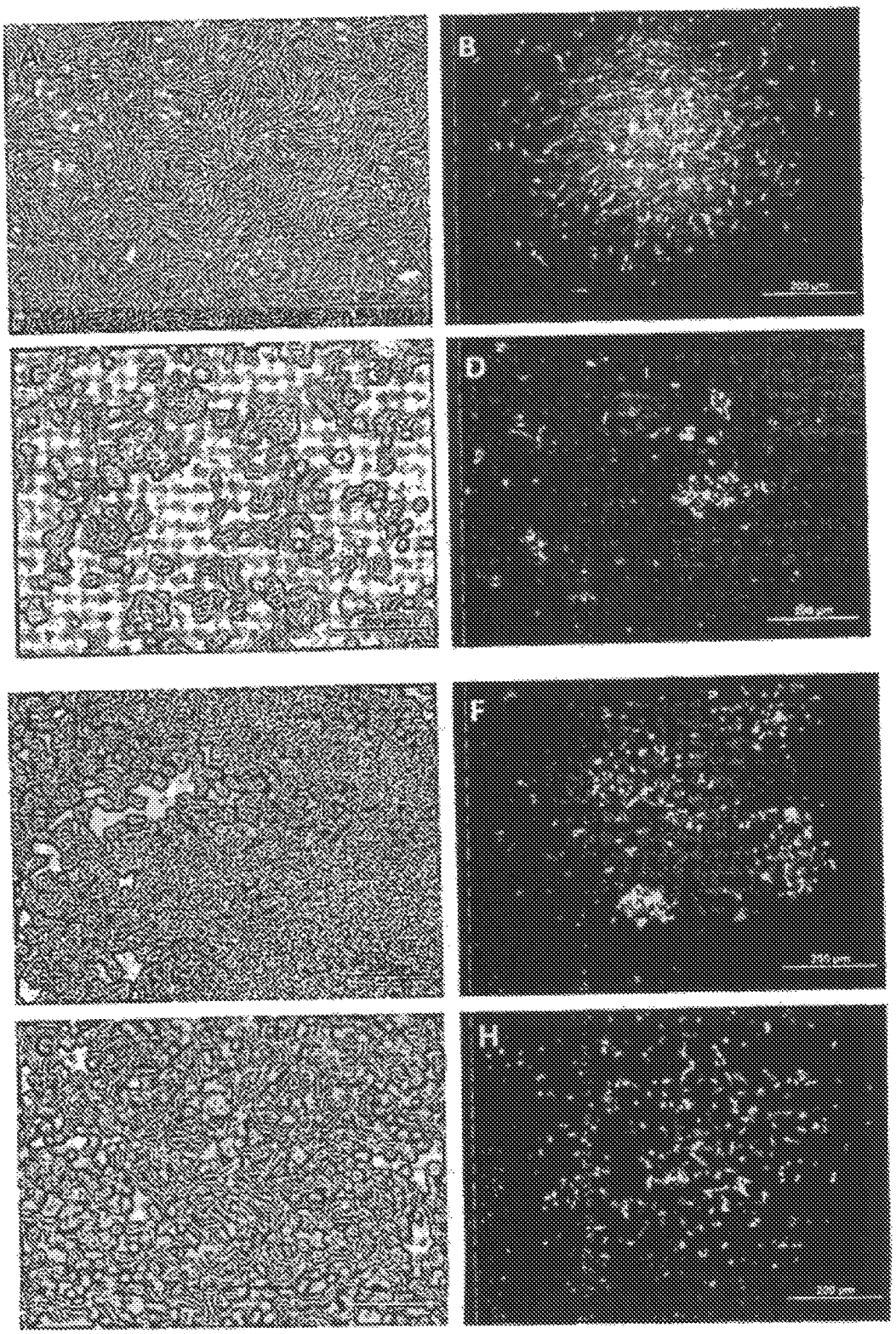
FIG. 7 shows recombinant cell lines modified with the vector p1054-rFVII; phase-contrast imaging showing in A, C, E and G the BHK-21, HepG2, HKB-11 and Sk-Hep cell lines, respectively; phase-contrast imaging showing the expression of the GFP gene in the BHK-21 (B), HepG2 (D), HKB-11 (F) and Sk-Hep (R) lines, FIG. 8 graphically depicts the relative expression of the recombinant factor VII gene in human cell lines.

In order to verify the success of the modification of the cell lines, photomicrographs in a fluorescence optical microscope were also made (FIG. 7).

Characterization of Recombinant FVII Produced by Cell Lines

Expression of rFVII in Modified Cell Lines

Figure 8:
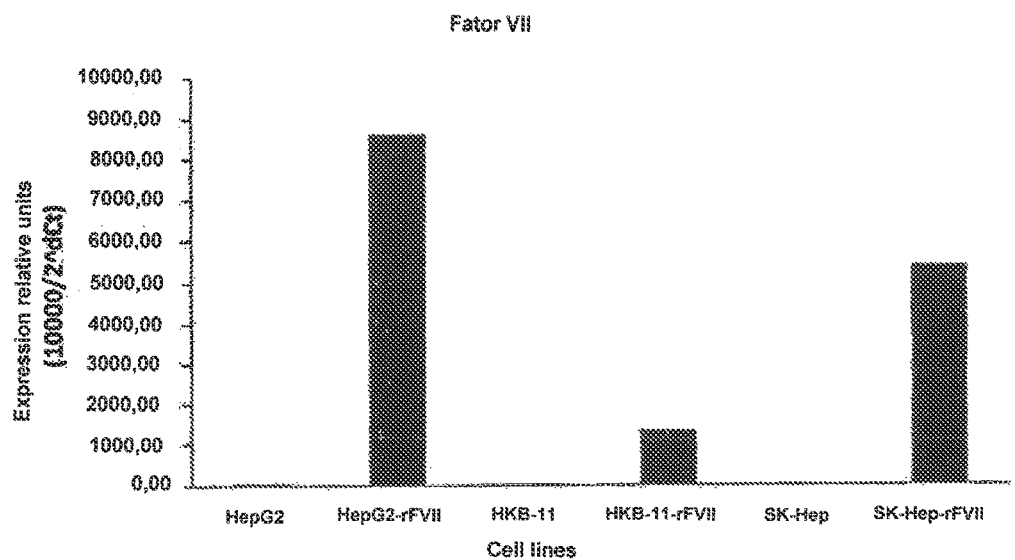

After confirming the expression of the GFP gene by the flow cytometry and fluorescence microscopy methodologies, the next step consisted of analyzing mRNA expression related to the factor VII gene in human cell lines, HepG2, HTB-11 and Sk-Hep (FIG. 8).

As can be seen in FIG. 8, the expression of mRNA relative to the factor VII gene from the three human cell lines was in the order of 8589 expression relative units (ERU) in HepG2-rFVII, 1361 ERU in HKB-11-rFVII line and 5357 ERU in Sk-Hep-rFVII cells.

These data show not only the efficiency in the modification of the cell lines but also the ability of these lines in expressing the recombinant protein of interest.

Quantification of rFVII in Modified Cell Lines

In order to quantify the total rFVII (active and non-active) produced by the recombinant cell lines, the ELISA assay was performed. To quantify the biologically active rFVII (rFVIIa) produced by the modified cell lines, the coagulometric test of partial thromboplastin time (PTT) was performed. The results of both tests are shown in Table 2.

TABLE 2

Quantification of FVIIr by the ELISA and PTT assay

| Samples | Elisa (ng/mL) | Biological activity |
|---|---|---|
| HepG2 non-transduced | 6.3 | Nd |
| HepG2/FVIIr | 1176.57 (SD 465.65) | 1.02 (SD 0.19) |
| Sk-Hep non-transduced | 0.0 | Nd |
| Sk-Hep/FVIIr | 702.36 (SD 59.42) | 2.22 (SD 1.20) |
| HKB-11 non-transduced | 0.0 | Nd |
| HKB-11/FVIIr | 585.44 (SD 128.08) | 0.17 (SD 0.05) |
| BHK21 non-transduced | 0.0 | Nd |
| BHK-21/FVIIr | 222.60 (SD 112.71) | 0.16 (SD 0.04) |
| Human plasm | 500.0 | 1.0 |

As can be seen, the three human cell lines HepG2-rFVII, Sk-Hep-rFVII and HKB-11-rFVII showed amounts of rFVII levels higher than those found in human plasma, of the order of 1.7×, 1.5×, and 1.35×, respectively, showing that these lines are promising to produce the recombinant protein.

In relation to actively produced rFVII, Sk-Hep/rFVII is the cell with the ability to produce more biologically active protein, followed by HepG2/rFVII, HKB-11/rFVII and finally the murine cell line BHK-21/rFVII.

Western Blot

After quantifying the recombinant protein by ELISA and verifying that the cell lines were producing biologically active FVIIr, a Western Blot was carried out to observe the size of the protein produced.

After checking the band pattern on the polyacrylamide gel, blotting was performed. For this, the gel content was transferred to a PVDF membrane and labeled with an anti-FVII antibody (FIG. 9).

Figure 9:
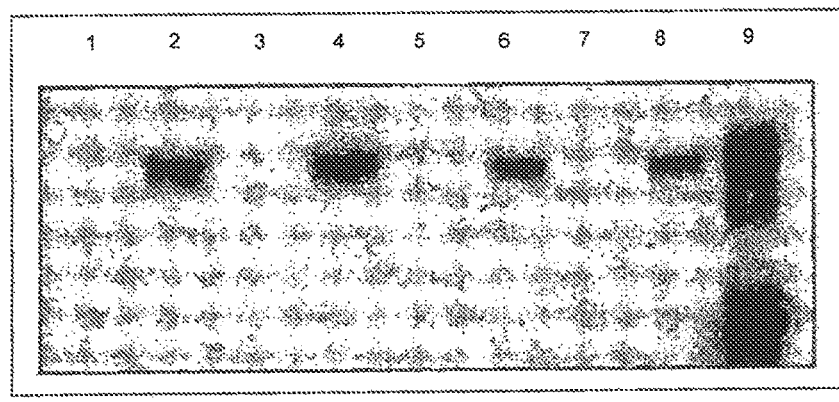
FIG. 9 shows Western Blot; 1—non-transduced HepG2, 2—HepG2/FVIIr, 3—non-transduced Sk-Hep-1, 4—Sk-Hep-1 FVIIr, 5—non-transduced HHK-11, 6—HKB-11/FVIIr, 7—non-transduced BHK-21, 8—BHK-21/FVIIr, 9—Novo Seven.

As can be seen in FIG. 9, the bands of approximately 55 kDa evidenced the expression of the recombinant protein in the modified cell lines (lanes 2, 4, 6 and 8), whereas there is no expression of FVIIr in non-transduced cells (lanes 1, 3, 5, 7).

It can also be observed that cells with higher mRNA expression related to FVIIr, as well as greater quantification in ELISA, are the cells that present bands of greater intensity in the Western Blot (HepG2-FVIIr on lane 2 and Sk-Hep-1-FVIIr on lane 4). Similarly, cells with lower mRNA expression and lower quantification in the ELISA, present bands related to FVIIr of weaker intensity values in Western Blot (HKB-11-FVIIr on lane 6 and BHK-21-FVIIr on lane 8), On lane 9 the Novo Seven that was used as positive control of the reaction can be observed. The higher molecular weight band refers to unactivated single chain FVII (50 KDa), and the lower weight band (20 KDa) refers to the activated FVIIr light chain. The band of 30 KDa, referring to the heavy chain of FVIIr, does not appear in blotting since a monoclonal antibody that does not label this chain specifically was used.

Generation of Homogenous HKB-11/rFVII Population

As shown previously, the HKB-11 cell line was the one that presented the lowest modification efficiency, only 32% of the cells were expressing the GFP marker gene, whereas the Sk-Hep, HepG2 and BHK-21 expressed 95%, 73% and 80%, respectively.

After 12 months of culture, necessary for the establishment of cell lines, the percentage of cells that expressed GFP was as follows (Table 3).

TABLE 3

Decrease in GFP percentage after 12 months of culture

| Cell line | % of GFP after transduction | % of GFP after 12 months of culture |
|---|---|---|
| Sk-Hep-rFVII | 95% | 80% |
| HKB-11-rFVII | 32% | 16% |
| HepG2-rFVII | 73% | 50% |
| BHK-21-rFVII | 80% | 64% |

As can be seen in. Table 3, the HKB-11 cells were those that presented greater loss in the expression of the GFP marker gene, around 50%.

Figure 10:
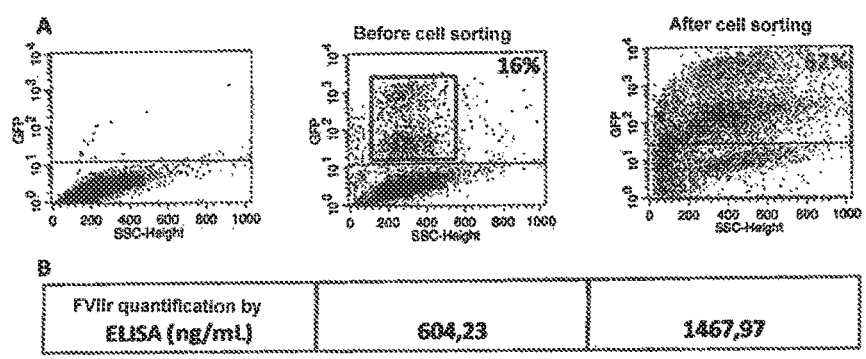
FIG. 10 graphically depicts GFP expression and quantification of FVIIr in the recombinant cell line HKB-11 before and after sorting—In graphic A showing size (FSC) by internal complexity (SSC), followed by the GFP expression graphic in the cell lines modified before the sorting; from the gate performed, in the last graphic an enrichment can be seen in the number of cells expressing GFP after the cell sorting—in B, quantification of FVIIr by ELISA, before and after cell sorting.

To generate a more homogeneous population and with levels of expression more comparable to other cell lines shown in this invention, the selection of positive GFP HKB-11 cells was performed by cell sorting, which is shown in FIG. 10.

As observed, there was an increase in the number of cells that express GFP in the order of 3.9 times. These data were also confirmed by fluorescence microscopy.

In addition to the increase in the percentage of positive GFP cells, it was possible to observe an increase in the amount of rFVII produced, when the supernatant was assayed by ELISA test. After a period of 96 hours of culture, non-sorting cells were producing 604 ng/ml, of rFVII, while the post-sorting cells, cultured under the same conditions, produced 1468 ng/mL. From these results, the following experiments were conducted only using post-sorting HKB-11/rFVII cells, cited as HKB-11/rFVII.

Characterization of rFVII-Producing Cell Lines

To date, results have been presented relating to the generation of recombinant FVII-producing cell lines, as well as an overall characterization of the protein at the level of expression, biological activity and western blot.

The following results refer to the characterization of the recombinant cell lines to select the best rFVII producer.

Modified Cell Lines Express rFVII mRNA and γ-Carboxylation Enzymes

Initially, mRNA expression analysis was performed related to the factor VII gene and the γ-carboxylase enzymes, VKORC1 and calumenine.

In order to analyze the expression profile, only the human cell lines HepG2, HKB-11 and Sk-Hep in four different conditions were used: 1) without transduction and treatment with vitamin K, 2) without transduction and treated with 5 µg/mL vitamin K, 3) transduced with vector 1054-rFVII and without treatment with vitamin K and 4) transduced with 1054-rFVII vector and treated with 5 µg/mL vitamin K.

After analyzing the data, it can be observed that the three human lines presented mRNA expression related to recombinant FVII, after lentiviral vector transduction. When submitted to the treatment with vitamin K for a period of 10 passages in culture, the cells showed a similar expression (HepG2: 164563 URE, HKB-11: 119122 ERU and Sk-Hep: 124919 ERU) demonstrating a stabilization in the expression levels of the recombinant protein (FIG. 11).

It is possible to observe that non-transduced HepG2 cell line, because it is derived from a hepatocarcinoma, expresses levels of endogenous FVII mRNA (as shown above) and that the expression of this endogenous FVII is increased by 480 fold when cells are treated with vitamin K.

When the expression of the enzymes related to γ-carboxylation was analyzed, it was possible to observe that there was a difference in the expression levels of γ-carboxylase enzymes, VKORC1 and the inhibitor calumenine (FIG. 11).

Figure 12:
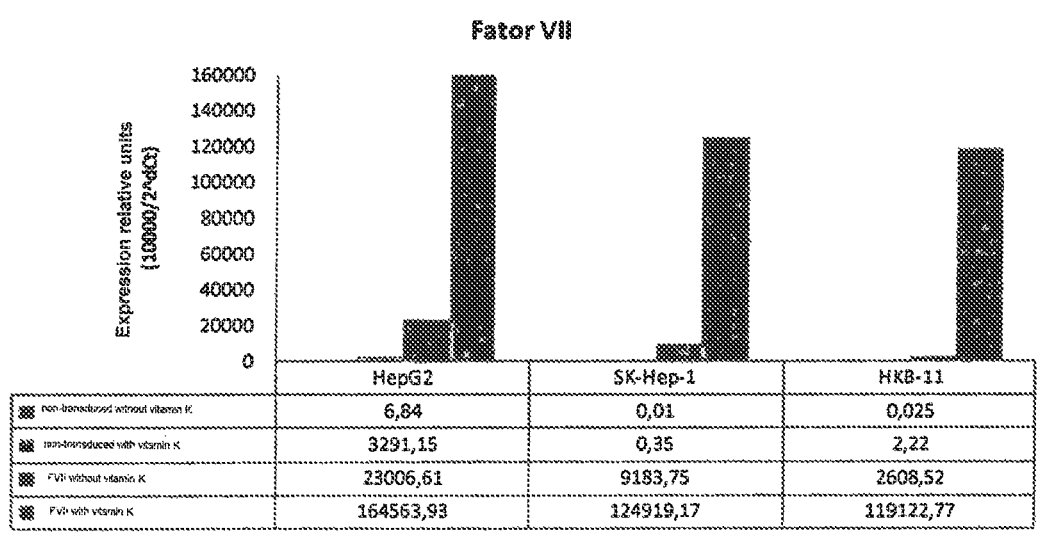

As seen in FIG. 12, when the cells were treated with 5 ug/ml vitamin K, there was an increase in the expression level of enzymes. When comparing treated and untreated non-transduced cells, it can be observed that in HKB-11 cells the expression of mRNA of the VKORC1 gene increased 43-fold (from 64 to 2788 ERU); γ-carboxylase expression increased 351-fold (from 20 to 7030 ERU) and the expression level of calumenine mRNA increased 409 fold (from 41 to 16783 ERUs). In SK-Hep-1 cells, the expression of the mRNA of VKORC1 gene increased 91 fold (from 10 to 914 ERU), γ-carboxylase increased 416 fold (from 12 to 4989 ERU) and the calumenine inhibitory gene increased 397 fold (from 30 to 11922 ERU). In HepG2 cells, the expression of the mRNA of the VKORC1 gene increased 98 fold (from 104 to 10172 ERUs); γ-carboxylase expression increased 220 fold (from 72 to 15880 ERU) and the level of mRNA expression of the calumenine increased 211 fold (from 55 to 11612 ERU).

The same pattern of expression can be observed in the cell lines modified with FVII before and after treatment with vitamin K. In the HKB-11-FVII cell line the expression of the VKORC1 mRNA increased 7 fold (from 418 to 2883 ERU), γ-carboxylase increased 150 fold (from 59 to 8869 ERU) and the expression level of calumenine gene mRNA increased 54 fold (from 318 to 17244 ERU). In the Sk-Hep-1-FVII cells the expression of γ-carboxylase increased 108-fold (from 41 to 4416 ERU) and the expression level of calumenine mRNA increased 54 fold (from 267 to 14331 ERU). In HepG2-FVII cells a 4 fold increase of the expression of VKORC1 (from 2045 to 8491 ERU) was observed, the expression of γ-carboxylase mRNA increased 58 fold (from 197 to 11443 ERU) and the expression level of calumenine gene mRNA increased 12 fold (from 1317 to 15621 ERU).

Growth Kinetics of Recombinant Cell Lines

To evaluate the growth profile of recombinant factor VII-producing Sk-Hep, HBK-11 and BHK-21 cell lines the experiments were carried out for a period of 7 days, in duplicate.

Figure 13:
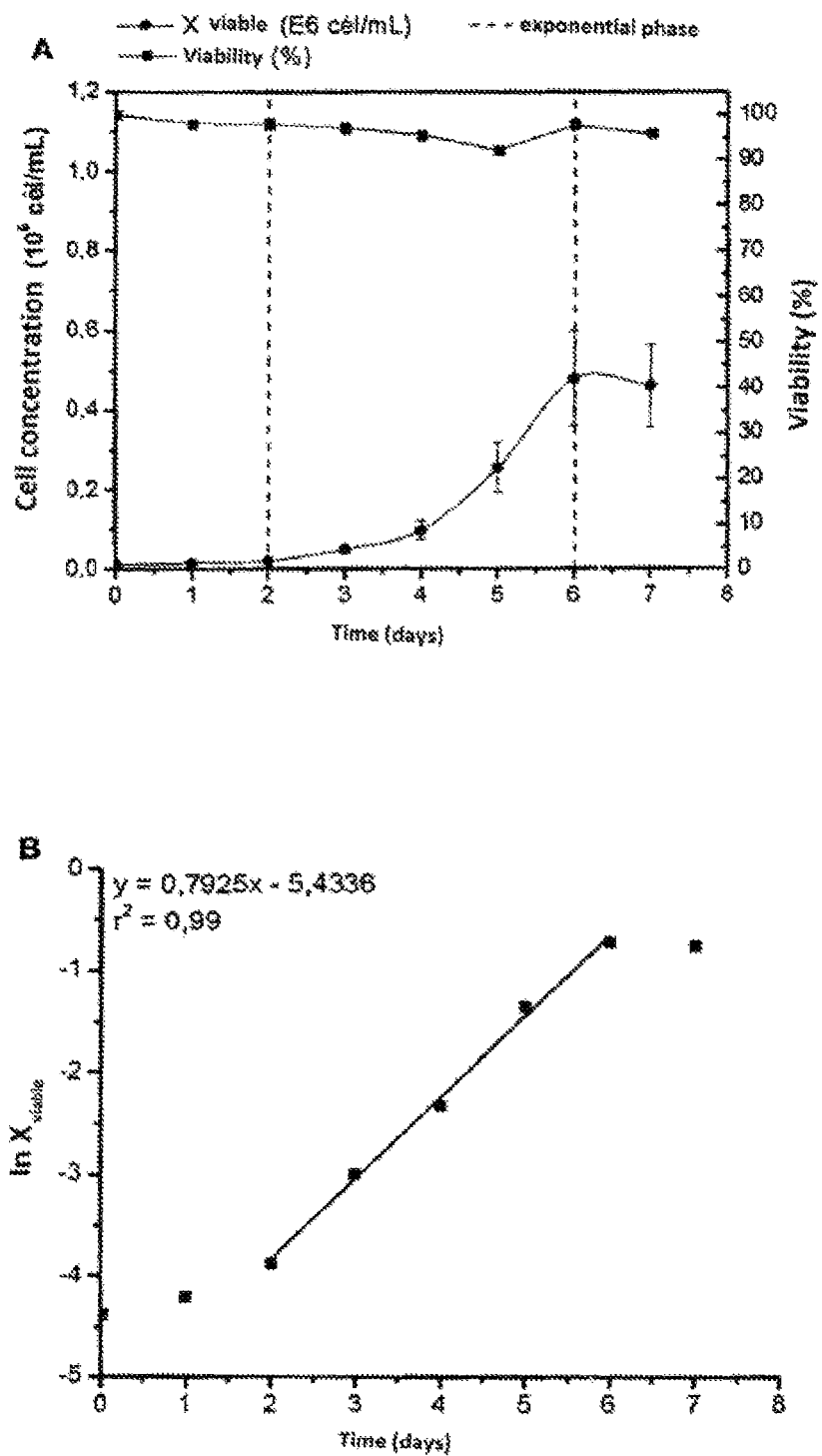
FIG. 13 graphically depicts the growth kinetics of SK-Hep-1-FVIIr cell line in A, cell growth and viability during the culture of Sk-Hep-1-FVIIr cells in DMEM medium with 10% FBS, in 10 cm$^2$ plates; in B, the specific maximum growth rate ($\mu_{max}$=0.79 day$^{-1}$) (n=2).

FIG. 13 allows us to observe that the Sk-Hep cell presented high viability, around 95%, throughout the whole analyzed period. The maximum cell concentration was $0.48 \times 10^6$ cells/mL achieved on the sixth day of experiment. The exponential phase of growth occurred between days 1 and 6 and the maximum specific growth rate ($\mu_{max}$) was 0.72 day$^{-1}$. It can be observed that after this period there is still cell growth, however, at a lower rate.

Figure 14:
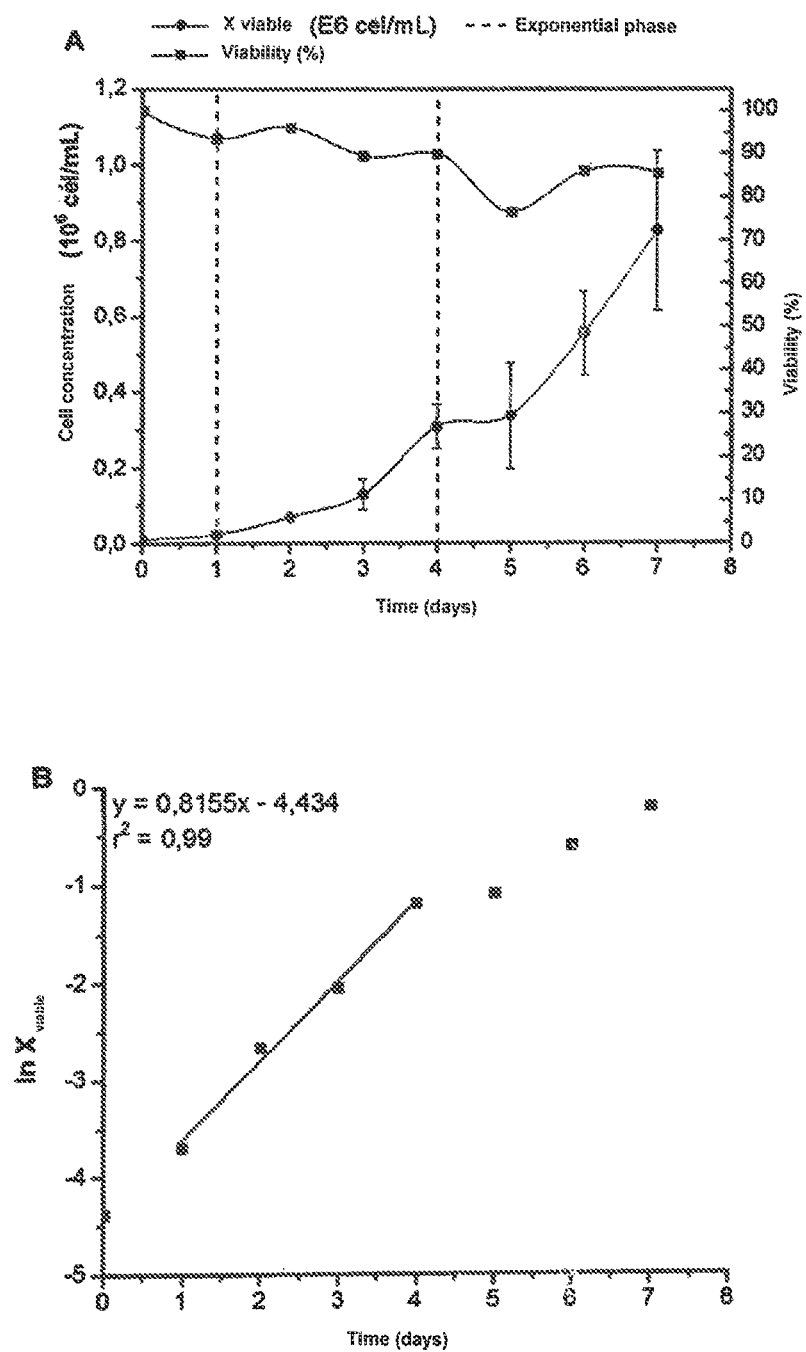
FIG. 14 graphically depicts the growth kinetics of HKB-11-FVIIr-A cell line, cell growth and viability during the culture of HKB-11-1-FVIIr cells in DMEM-F12 medium with 10% FBS, in 10 cm$^2$ plates; in B, specific maximum growth rate ($\mu_{max}$=0.81 day$^{-1}$) (n=2).

With the analysis of FIG. 14 showing the data related to HKB-11 cell line, it was possible to observe that these cells presented viability, around 90%, during the first four days of experiments, followed by about 80% in the last three days. The maximum cell concentration was $0.82 \times 10^6$ cells/mL achieved on the seventh day of the experiment. The exponential phase of growth occurred between days 0 and 4 and the maximum specific growth rate ($\mu_{max}$) was 0.80 day$^{-1}$.

Figure 15:
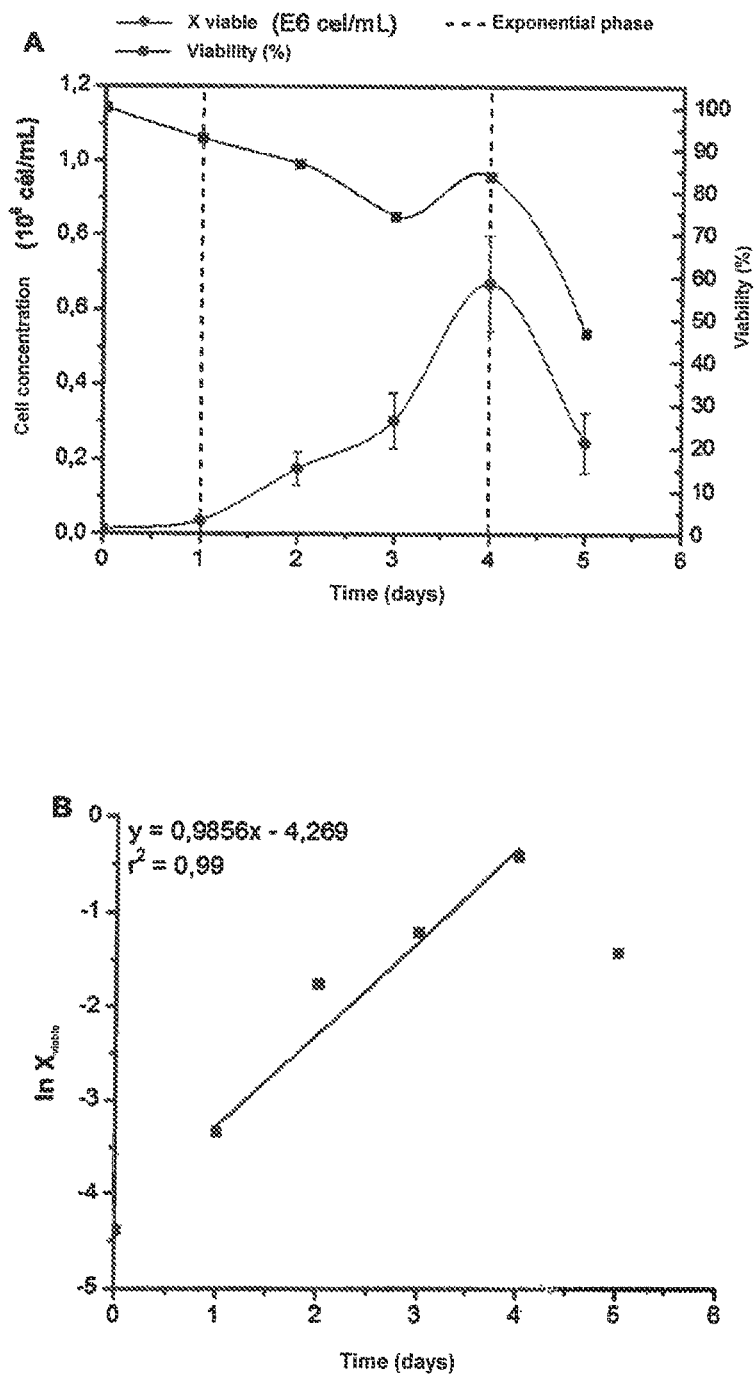
FIG. 15 graphically depicts the growth kinetics of BHK-21-FVIIr-A cell line, cell growth and viability during the culture of BHK-21-1-FVIIr cells in EMEM medium with 10% FBS, in 10 cm$^2$ plates; in B, the specific maximum growth rate ($\mu_{max}$=0.98 day$^{-1}$) (n=2).

Subsequently, the data from the BHK-21 cell was analyzed (FIG. 15).

The BHK-21 murine line (FIG. 15) showed a viability of around 92% on the first day, which declined during the experiment, leading to cell death on the sixth day. The maximum cell concentration was $0.67 \times 10^6$ cells/mL achieved on the fourth day of experiment. The exponential growth phase occurred between days 0 and 4 and the maximum specific growth rate ($\mu_{max}$) was 1.0 day$^{-1}$. After this period, the cells entered the process of cell death.

Production Kinetics of rFVII in Cell Lines

In addition to the growth curve, assays in a 100 mm$^2$ plate with the same cell lines were also performed to evaluate the production of recombinant factor VII. To this end, the initial concentration of cells was higher than that used in growth kinetics experiments.

FIG. 16 shows a graphic of the concentration of FVII (ng/mL) over time, of the three human cell lines and the murine line BHK-21.

When analyzing the amount of rFVII after the experimental period, it was possible to observe that HepG2 cells showed a higher production of recombinant protein, while in 24 h there was a production of 1227 ng/mL, after 96 h of culture, production reached 1843 ng/mL. As the cells were cultured in 8 ml of medium, it was possible to produce a total of 14.7 µg of rFVII, which corresponds to 29.5 IU.

Sk-Hep cells had a production of 415 ng/mL in 24 h, reaching a total of 1432 ng/mL after 4 days. The HKB-11 line showed a similar production profile when compared to Sk-Hep, on the first day there was an amount of 435 ng/ml of rFVII and at the end of 96 h it was possible to quantify about 1468 ng/mL. As there were 8 ml of culture medium in the plate, it was possible to produce a total of 11.7 µg of rFVII, which corresponds to 23.5 IU from the cells HKB-11 and 11.4 µg of rFVII, corresponding to 22.9 IU from Sk-Hep cells.

The BHK-21 murine cell line was the line with the lowest production of rFVII throughout the experiment, since in 24 hours there was 250 ng/ml and at the end of 96 hours only 449 ng/mL, totaling in 8 mL a production of 3.6 µg of rFVII, which corresponds to 7.2 IU.

Production of rFVII in Sk-Hep and HKB-11 Cell Lines in Spinner Flasks and Bioreactors Analysis of the previous results showed that the HepG2 cells have an extremely slow growth pattern, which made it impossible to use them in the subsequent stage of the work. The BHK-21 cell line, of murine origin, is not the focus of the present invention, being used only as a control. The two FVIIr-producing human cell lines, which were used for subsequent experiments of suspension culture were Sk-Hep-1-FVIIr and HKB-11-FVIIr.

The experiments were carried out for a period of 10 days to analyze the growth profile, as well as the production of FVIIr in the cell lines growing in suspension using microcarriers in spinner flasks and in a stirred tank bioreactor.

Figure 17:
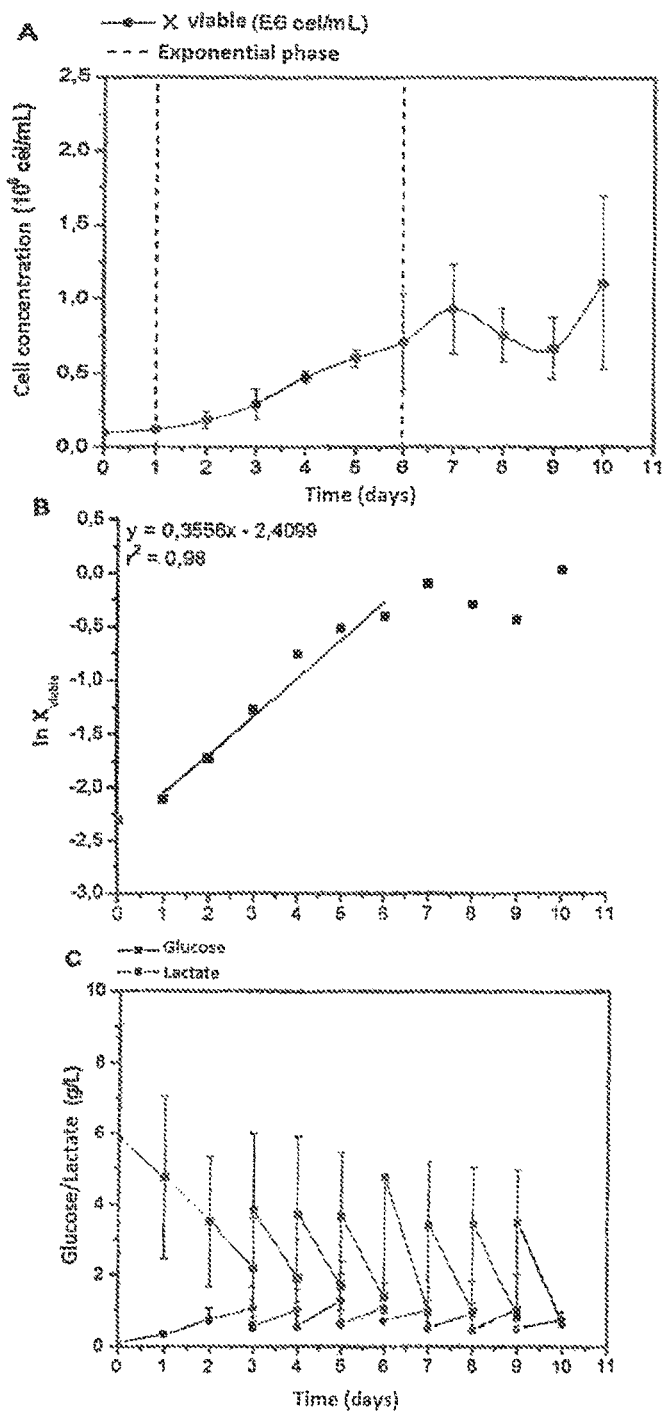

Analyzing our data it was possible to observe that the Sk-Hep-1-FVIIr cell reached the maximum cellular concentration, $1.11 \times 10^6$ cel/mL, on the tenth day of the experiment. The exponential phase of growth occurred between days 1 and 6 with a $\mu_{max}$ of 0.35 day$^{-1}$ (FIG. 17).

During the 10 days of culture it was possible to observe a gradual consumption of glucose, as expected, however, there was no complete depletion due to 50% changes in the culture medium every 24 hours. In relation to lactate production, it was observed that this reached the maximum concentration on the fifth day of culture, with a mean value of 1.25 g/L (FIG. 17).

Figure 18:
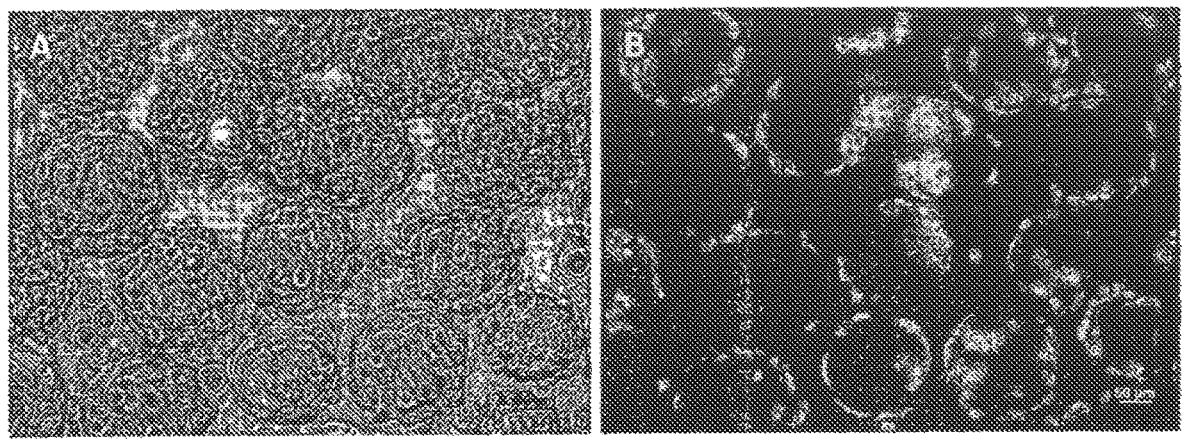
FIG. 18 shows the morphology of Sk-Hep-1-FVIIr cells adhered on microcarriers on the seventh day of experiment—in A, photomicrography in phase contrast, showing the cells adhered on microcarriers; in B, photomicrography of fluorescence showing the GFP expression in the adhered cells.

To illustrate the culture in microcarriers and expression of the GFP marker gene, images were taken with microscopy of phase contrast and fluorescence, as shown in FIG. 18.

Figure 19:
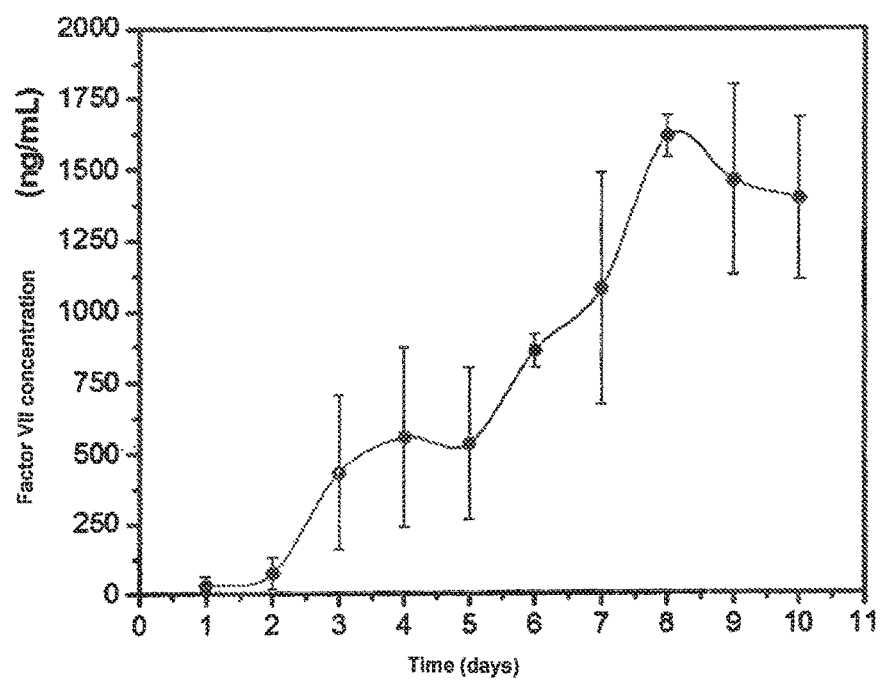
FIG. 19 graphically depicts the production kinetics of recombinant factor VII producing Sk-Hep-1 cell line cultured in spinner flasks for 10 days, FIG. 20 graphically depicts the biological activity of FVIIr produced by the Sk-Hep-1-FVIIr cell line in spinner flasks for 10 days.

In order to quantify the production of FVIIr by the Sk-Hep-1-FVIIr cell, an ELISA assay was performed. As shown in FIG. 19, the production reached its maximum peak on the eighth day of experiment, an average concentration of 1615 ng/ml (DP 74.47) of FVIII. At the end of 10 days, a mean production of 4052 ng/ml of the recombinant protein in a volume of 50 mL was obtained, totaling a production of 202.6 µg FVIIr, which corresponds to approximately 405 IU. The productivity ($C_{max}$/t) in the Sk-Hep-1-FVIIr cell was 201.8 ng/mL/day.

Figure 20:
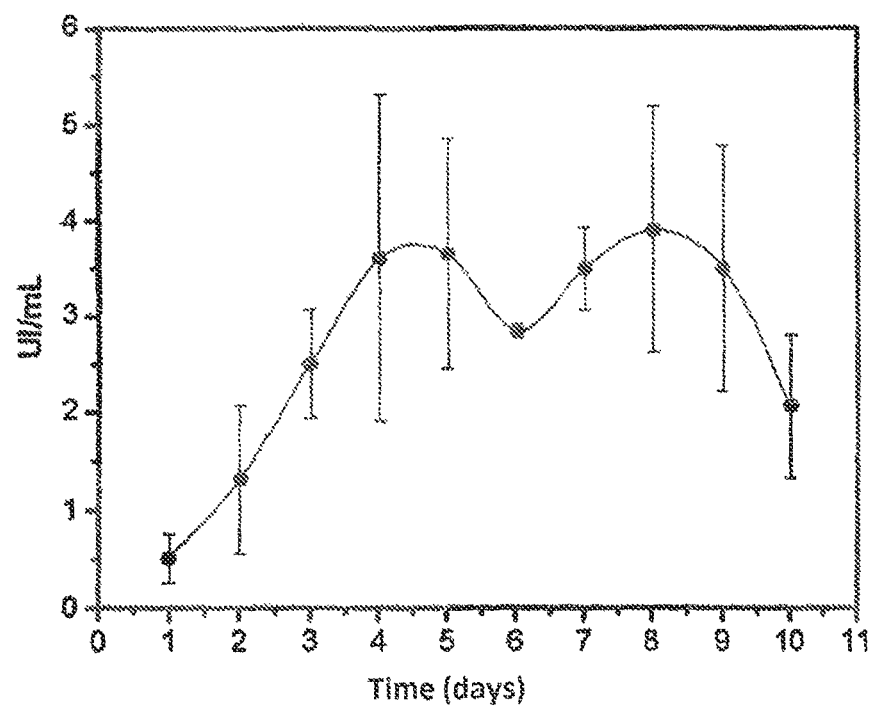

The kinetics of recombinant protein production was also measured in terms of the amount of biologically active FVIIr produced by the cells. FIG. 20 shows that there was a peak of production of biologically active FVIIr on the eighth day of culture, in the order of 4 IU/ml.

Figure 21:
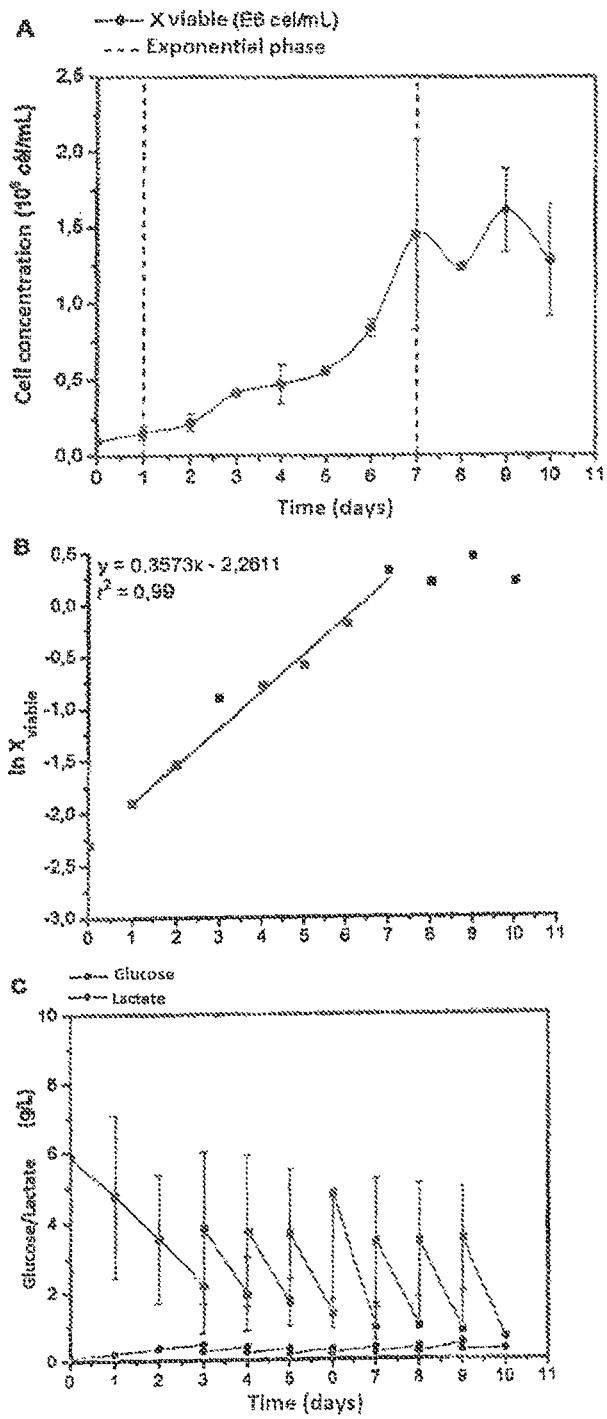
FIG. 21 graphically depicts the culture of the HKB-11-FVIIr cell line in microcarriers in spinner flasks in DMEM-F12 medium 10% FBS (n=2)—cell growth (A), specific maximum growth rate (B) and concentration of glucose and lactate during the culture.

When analyzing the HKB-11-FVIIr cells, these reached the maximum cell concentration, $1.61 \times 10^6$ cells/mL, on the ninth day of the experiment. The exponential growth phase occurred between days 1 and 7 with a $\mu_{max}$ of 0.36 day$^{-1}$ (FIG. 21).

As in Sk-Hep-1 cells, over the 10 days of culture it was possible to observe a gradual consumption of glucose, as was expected, however, there was no complete depletion due to the 50% changes in culture medium every 24 hours. Regarding the production of lactate, it was observed that it reached the maximum concentration on the ninth day of culture, with a mean value of 0.47 g/L (FIG. 21).

Figure 22:
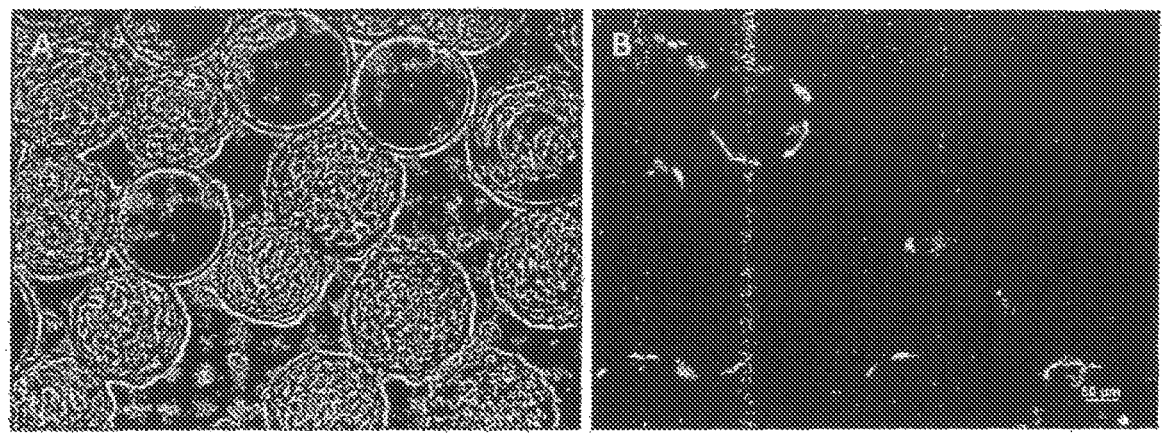
FIG. 22 shows the morphology of adhered HKB-11-FVIIr cells in microcarriers on the seventh day of experiment—in A, photomicrography in phase contrast, showing the cells adhered to microcarriers; in B, photomicrography of fluorescence showing GFP expression in adhered cells.

Once more, to illustrate the culture in microcarriers and expression of the GFP marker gene were made images with phase contrast microscopy and fluorescence of the cell HKB-11-FVIIr, as shown in FIG. 22.

Figure 23:
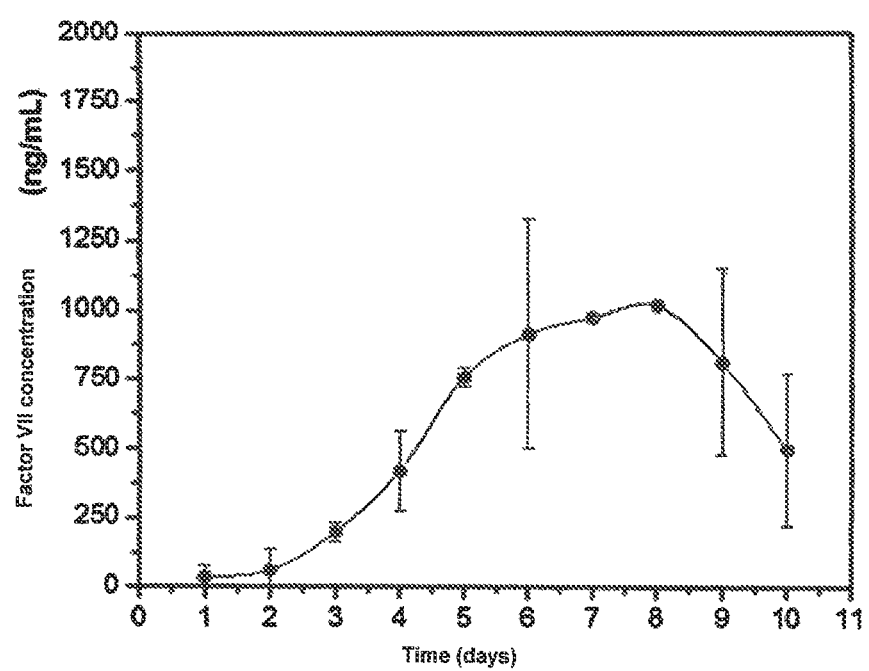
FIG. 23 graphically depicts the production kinetics of the recombinant factor VII HKB-11 cell line cultured for 10 days in spinner flasks.

The ELISA assay was also performed for the HKB-11 line. As shown in FIG. 23, production had its maximum peak reached on the eighth day of the experiment, reaching an average concentration of 1020 ng/ml (SD 9.8) of FVIIr. At the end of 10 days, a mean concentration of 3038 ng/mL FVIIr was achieved in 50 mL of culture medium, totalizing a production of 152 µg of FVIIr, which corresponds to about 304 IU. The productivity ($C_{max}$/t) in the HKB-11-FVIIr cell was 127.5 ng/mL/day.

Figure 24:
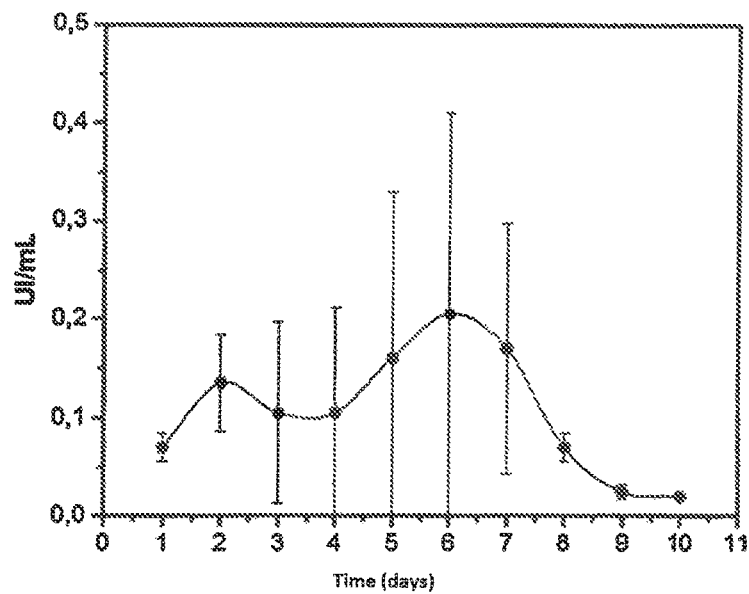
FIG. 24 graphically depicts the biological activity of FVIIr produced by the HKB-11-FVIIr cell line in spinner flasks for 10 days.

The kinetics of recombinant protein production was also measured in terms of the amount of biologically active FVIIr produced by the cells. FIG. 24 shows that there was a peak of production of biologically active FVIIr on the sixth day of culture, in the order of 0.2 IU/mL.

Production of rFVII in Sk-Hep Cell Lines in Bioreactor (Stirred Tank)

| Sk-Hep-FVII cell supernatant | Concentration of rFVII (µg/mL) |
| --- | --- |
| T75 cm$^2$ T-flask(15 mL) | 0.7 |
| Spinner (50 mL) | 1.6 |
| Biorreator (1 L) | 72.7 |
| Suspension culture | 0.014 |

The table shows the concentration of rFVII, in µg/mL, quantified by the ELISA method secreted by Sk-Hep-FVII cell supernatant under four different culture conditions:

1) 75 cm$^2$ T flasks containing 15 mL DMEM medium supplemented with 10% fetal bovine serum, which resulted in a rFVII concentration of 0.7 µg/mL;

2) spinner flasks using microcarriers containing 50 ml of DMEM medium supplemented with 10% fetal bovine serum, which resulted in a rFVII concentration of 1.6 µg/mL;

3) stirred tank bioreactor using 1 L of DMEM medium supplemented with 10% fetal bovine serum which resulted in a rFVII concentration of 72.7 µg/mL; and 4) suspension culture in Erlenmeyer flasks using serum free medium which resulted in a rFVII concentration of 0.014 µg/mL.

From the analysis of the results it can be observed that when cultured in a bioreactor with controlled temperature of about 35° C. to 40° C. preferably 37° C., pH of about 7 to 7.8, preferably 7.4, dissolved oxygen of about 15% to 25%, preferably 20% and agitation conditions of about 40 to 60 rpm, preferably 50 rpm, the Sk-Hep cells were able to secrete 45 times more recombinant FVII when compared to spinner flask culture.

Adaptation of Factor VII-Producing HKB-11 Cell Line to Growth in Suspension in Bovine Fetal Serum Free Medium Because of the higher productivity, the HKB-11/rFVII cell was selected for the adaptation to the growth in suspension in serum free medium, and subsequent culture in bioreactors for the production of rFVII in large scale.

Figure 25:
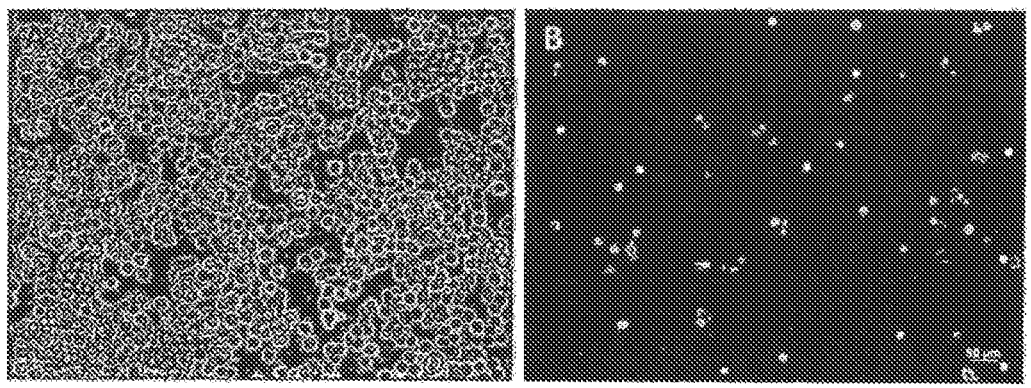
FIG. 25 shows the morphology of HKB-11/rFVII cells in a third passage in bovine fetal serum-free medium; in A, photomicrography in phase contrast, showing the cells adapted to the growth in suspension; in B, photomicrography of fluorescence showing the GFP expression in the adapted cells.

As shown in FIG. 25, the rounded cell morphology, the formation of cell clusters, together with the viability greater than 85%, is indicative that the cells were adapted to growth in suspension.

These results show that this cell line is an excellent candidate for rFVII production on an industrial scale, as it presents a higher production than the commercially available BHK.

The invention claimed is:

1. A process for modifying human cell lines to produce increased levels of blood coagulation Factor VII (FVII) in large scale, comprising the steps of:
   (1) providing viral particles containing a FVII cDNA having a nucleotide sequence that is at least 90% identical to SEQ ID NO: 1, and a selectable marker, wherein the viral particles are produced by transfecting a Hek293T cell line;
   (2) stably transducing human cell lines selected from SK-Hep 1, HKB11 and HepG 2 with the viral particles to form human FVII producing cells; and
   (3) culturing the human FVII producing cells from step (2) using static conditions and/or in suspension with/without microcarriers and a stirred tank bioreactor.

2. The process according to claim 1, wherein the viral particles produced from the Hek293T cell line expresses a SV40 T antigen.

3. The process according to claim 2, wherein the transfection is performed in a polyethylamine reagent with three plasmids in the following ratio: 10 to 20 μg vector with transgene p1054-rFVII; 8 to 15 μg pCMVΔR8.91; and 5 to 10 μg pMD2 VSVG.

4. The process according to claim 1, wherein the selectable marker is an antibiotic resistance gene which is selected from the group consisting of hygromycin, neomycin, aminoglycoside phosphotransferase, bleomycin and a derivative selected from the group consisting of xanthine-guanine phosphoribosyltransferase and glutanic-pyruvate transamine, phleo, bleo, zeocin, and Xanthine-guanine phosphoribosyltransferase, and an aminonucleoside antibiotic selected from the group consisting of: puromycin and a fluorescent protein.

5. The process according to claim 1, wherein before the transducing in step 2, the cells are plated in a concentration of 2×10⁵ cells per well in a 6-well plate and viral concentration of 1 to 10 virus/cell is added, based on viral titration values.

6. The process according to claim 1, wherein in step (3) the cells are cultured in culture flasks for expansion, incubated at 37° C. and 5% $CO_2$ until confluence of 80%; released with Trypsin-EDTA and inoculated in flasks, after reaching a number of 5×10⁶ cells; and are inoculated in a bioreactor already containing culture medium and microcarriers.

7. The process according to claim 2, wherein the FVII cDNA and the selectable marker are separated by an internal ribosome entry site (IRES) element.

8. The process according to claim 1, wherein the human FVII producing cells of step 3 are cultured in serum-free or in serum-containing medium.

9. The process according to claim 8, wherein the serum-free medium is supplemented with a compound selected from the group consisting of: insulin, glutamine, ferric sulfate, synperonic, Insulin-Transferrin-Selenium, Sodium Pyruvate, Pluronic F68, a Lipid Supplement, a Cholesterol Supplement, an Amino Acid Solution, and 2-Mercaptoethanol.

10. The process according to claim 1, wherein the human cell line comprises SK-Hep-1 cells, wherein step 2 is carried out in a large scale with a bioreactor, and wherein the SK-Hep-1 cells secrete 45 times more human FVII when compared to a spinner flask culture.

11. The process according to claim 8, wherein the SK-Hep-1 cells produce blood coagulation Factor VII in a stirred tank bioreactor using medium supplemented with fetal bovine serum with a controlled temperature of about 35° C. to 40° C., pH of about 7 to 7.8, dissolved oxygen of about 15% to 25%, and agitation conditions of about 40 to 60 rpm.

12. The process according to claim 5, wherein the fluorescent protein is green fluorescent protein (GFP).

\* \* \* \* \*